US006077995A

United States Patent [19]
Upchurch et al.

[11] Patent Number: 6,077,995
[45] Date of Patent: Jun. 20, 2000

[54] FUNGAL GENE ENCODING RESISTANCE TO THE PHYTOTOXIN CERCOSPORIN

[75] Inventors: Robert G. Upchurch, Cary; Terrence M. Callahan, Raleigh; Marilyn Ehrenshaft, Cary, all of N.C.

[73] Assignees: The United States of America as represented by the Secretary of Agriculture, Washington, D.C.; North Carolina State University, Raleigh, N.C.

[21] Appl. No.: 08/620,077

[22] Filed: Mar. 21, 1996

[51] Int. Cl.[7] ............................. C12N 15/29; C12N 15/82; A01H 5/00; A01H 4/00
[52] U.S. Cl. ........................ 800/298; 800/295; 435/419; 435/320.1; 435/468; 435/69.1; 536/23.7; 536/24.1
[58] Field of Search ................................. 800/205, 295, 800/298; 435/419, 172.3, 69.1, 320.1, 468; 536/23.7, 24.1

[56] References Cited

U.S. PATENT DOCUMENTS 5,262,306  11/1993  Robeson et al. ........................... 435/29

OTHER PUBLICATIONS

Batchvarova et al. Phytopathology. vol. 82, No. 6, pp. 642–646, 1992.
Callahan et al. APS vol. 83, p. 1422, 1993.
Upchurch et al. Program, 18th Fungal Genetic Conference, Jun. 1995.
Bevan. Nucleic Acids Research vol. 12, No. 22, pp. 8711–8721, 1984.
Agrios, *Plant Pathology*, 3rd Edition, Academic Press, San Diego, CA, pp. 356–357 (1988).
Batchvarova et al., *Phytopathol.*, vol. 82, pp. 1477–1484 (1992).
Maniatis et al., *Molecular Cloning: A Laboratory Manual*, 8.49, 10.40–10.43 (1989).
Williamson et al., *Plant Physiol.*, vol. 88, pp. 1002–1007 (1988).
Sive et al., *Nucleic Acids Research*, vol. 16, p. 10937 (1988).
Straubinger et al., *Fungal Genetic. Newsl.*, vol. 39, pp. 82–83 (1992).
Roberts et al., *Curr. Genet.*, vol. 15, pp. 177–180 (1989).
Daub et al., *Phytopathology*, vol. 77, pp. 1515–1520 (1987).
Daub et al., *Light Activated Pesticides*, pp. 271–280 (1987).
Caballero et al., *Mol. Gen. Genet.*, vol. 230, pp. 401–412 (1991).
Coque et al., *EMBO J.*, vol. 12, pp. 631–639 (1993).
Ehrenhofer–Murray, *Mol. Gen. Genet.*, vol. 244, pp. 287–294 (1994).
Guilfoile et al., *J. Bacteriol.*, vol. 174, pp. 3651–3658 (1992).
Hofmann et al., *Chem. Hoppe–Seyler*, vol. 374, pp. 166–176 (1993).
Lomovskaya et al., *Proc. Natl. Acad. Sci.*, USA, vol. 89, pp. 8938–8942 (1992).
Neal et al., *Gene*, vol. 58, pp. 229–241 (1987).
Tennent et al., *J. Gen. Microbiol.*, vol. 135, pp. 1–10 (1989).
Varela et al., *Antimicrob. Agents Chemoth.*, vol. 37, pp. 1253–1258 (1993).
Zhang et al., *Molec. Microbiol.*, vol. 6, pp. 2147–2157 (1992).
Callahan and Upchurch, "The Light Induced Gene, LE6, from *Cercospora kikuchii* . . . ", American Society for Microb., Ann. Mtg., Wash., DC, May 1995.
Upchurch et al., "Transformation of the Fungal Soybean Pathogen . . . ", *App. and Environ. Microb.*, vol. 60(12), pp. 4592–4595 (1994).
Pathan et al., "Effects of *Cercospora kikuchii* on Soybean Seed . . . ", *Plant Disease*, vol. 73(9), pp. 720–723 (1989).
Orth, C., "Resistance of 17 Soybean Cultivars to Foliar, . . . ", *Plant Dis.*, vol. 78, pp. 661–664 (1994).
Upchurch etal., "Cercosporin efflux and partial auto–resistance . . . ", Program, 18th Fungal Genet. Conf., (Jun. 1995).
Callahan et al., "Sequence and Functional Analysis of Light . . . ", *APS*, vol. 83: 1422 (1993).
Callahan and Upchurch, "Promoter Analysis and Functional Determination . . . " ASM, Las Vegas, Am. Soc. of Microb., H–24, p. 204 (1994).
Hightower et al., "Electrophorectic karyotype of *Cercospora kikuchii*" vol. 27, pp. 209–292 (1995).
Ehrenshaft and Upchurch, "Host Protein(s) induces accumulation of the toxin cercosporin . . . ", *Phys. Molec. Plant Pathol.*, vol. 43, pp. 95–107 (1993).
Gordon–Kamm et al., "Transformation of Maize Cells . . . ", *The Plant Cell*, vol. 2, pp. 603–618 (1990).
Lowe et al., "Germline Transformation of Maize . . . ", *Biotechnology*, vol. 13, pp. 677–682, (1994).
Upchurch, R., "Genetic Regulation of Cercosprin Production . . . ", *JAOCS*, vol. 72(12), pp. 1435–1438 (1995).
Rollins et al., "Effects of Light– and Altered–cercosporin . . . ", Can. J. Microbiol., vol. 39, pp. 118–124 (1993).
Genetic Transformation System for the Fungal Soybean Pathogen *Cercospora kikuchii*, *Appl. Environ. Microb.*, pp. 2935–2939 (1991).
"Scientists Find Magic Bullet for Fungus Disease", *Bob Lewis's Farmletter*, Jan. 22, 1996.
Ehrenshaft and Upchurch, "Isolation of Light–Enhanced cDNAs of . . . " *Appl. Environ. Microb.*, pp. 2671–2676 (1991).
Lynch and Geoghegan, *Trans. Br. Mycol. Soc.*, vol. 69(3), pp. 496–498 (1977).

(List continued on next page.)

*Primary Examiner*—Douglas W. Robinson
*Assistant Examiner*—Thomas Haas
*Attorney, Agent, or Firm*—M. Howard Silverstein; John D. Fado; Gail E. Poulos

[57] ABSTRACT

The present invention is directed to nucleic acid and amino acid sequences which are responsible for moving the fungal toxin cercosporin across the plasma membrane of living cells. The DNA can be introduced into a plant using conventional methods of transformation in order to confer cercosporin resistance to plants.

21 Claims, 17 Drawing Sheets

OTHER PUBLICATIONS

Jenns et al., *Phytopathology,* vol. 79(2), pp. 213–219 (1989).

Okubo et al., "Biosynthesis of Cercosporin" *Agr. Biol. Chem.,* vol. 39(5), pp. 1173–1175 (1975).

Balis and Payne, "Triglycerides and Cercosporin from . . .", *Phytopathology,* vol. 61, pp. 1477–1484 (1971).

Fajola, *Physio. Plant Pathol.,* vol. 13, pp. 157–164 (1978).

Daub and Hangarter, *Plant Physiol.,* vol. 73, pp. 855–857 (1983).

Calpouzos and Stallknecht, *Phytopathology,* vol. 5, pp. 799–800 (1967).

Calpouzos, L., "Action of Oil in the Control of Plant Disease . . .", pp. 369–390 (1966).

Daub, ACS Symposium Series No. 339, Light Activated Pesticides, pp. 271–280, (1987).

Yamazaki and Ogawa, *Agr. Biol. Chem.,* vol. 36(10), pp. 1707–1718, (1972).

Lousberg et al., *Chemical Communications,* pp. 1463–1464 (1971).

Hopwood and Sherman, *Ann. Rev. Genet.,* vol. 24, pp. 37–66 (1990).

Daub, *Phytopathology,* vol. 72, pp. 370–374 (1982).

Kuyama et al., *The Pigment Cercosporin,* vol. 79, pp. 5725–5729 (1957).

Upchurch et al., *Appl. and Environ. Microb.,* vol. 57(10), pp. 2940–2945 (1991).

| FIG. 2a | FIG. 2b | FIG. 2c | FIG. 2d |

FIG. 2

```
gLE6  GCCGTCGAATGAGTTCCCTCATAGCAGTCTGGACCGGCTACTTTCCATACATTGACAATGACGAGCCCAGCGCGA  1200
cLE6  -----------------------------------------------CATACATTGACAATGACGAGCCCAGCGCGA
                                                     M  T  S  P  A  R gLE6  TCAACGCATACTGATACAGAGTCTCACGACGTCGTAAAGAGCGACTCGGAACTGGAAACTGGAGCACAGC  1275
cLE6  TCAACGCATACTGATACAGAGTCTCACGACGTCGTAAAGAGCGACTCGGAACTGGAAACTGGAGCACAGC
       S  T  H  T  D  T  E  S  H  D  V  V  K  S  D  S  E  S  K  L  E  H  S gLE6  GATTCGGATAATCAAGATGAGAAGTCCAAGCGCTAAGTTGGCGGAACGTCCTGAAGCCAGAGAAGATGAA  1350
cLE6  GATTCGGATAATCAAGATGAGAAGTCCAAGCGCTAAGTTGGCGGAACGTCCTGAAGCCAGAGAAGATGAA
       D  S  D  N  Q  D  E  K  S  N  A  K  L  A  E  R  P  E  A  K  P  E  E  D  E gLE6  GAACTCAATGATCAAGGCGAGAGGTACATCTGCGGCTGGCCCCTCTGGTATTTCTCTTGTTAGCCATGGTCTCCACA  1425
cLE6  GAACTCAATGATCAAGGCGAGAGGTACATCTGCGGCTGGCCCCTCTGGTATTTCTCTTGTTAGCCATGGTCTCCACA
       E  L  N  D  Q  G  E  R  Y  I  C  G  W  P  L  V  F  F  L  L  A  M  V  S  T gLE6  GTCTTCATTGTCGCTTTGAGCAACAATCAGCACACAGCACCATCACACACAGCGTTCAATAGTACC  1500
cLE6  GTCTTCATTGTCGCTTTGAGCAACAATCAGCACACAGCACCATCACACACAGCGTTCAATAGTACC
       V  F  I  V  A  L  S  N  T  I  I  S  T  A  I  P  A  I  T  T  A  F  N  S  T gLE6  CGAGATATTGGCTGGTACAACTCTGGAGAAGCTCTTGCAGCCACTGCCTTCCAACTACCTTTCGGGCGAGCGTAT  1575
cLE6  CGAGATATTGGCTGGTACAACTCTGGAGAAGCTCTTGCAGCCACTGCCTTCCAACTACCTTTCGGGCGAGCGTAT
       R  D  I  G  W  Y  N  S  G  E  A  L  A  A  T  A  F  Q  L  P  F  G  R  A  Y gLE6  CTCTTGATGGACCTGAAGTGGACTTTCCTCGTCTCACTGGCCTCCAGCCTGATCTGTGGCTGTG  1650
cLE6  CTCTTGATGGACCTGAAGTGGACTTTCCTCGTCTCACTGGCCTCCAGCCTGATCGGTCTGTGGCTGTG
       L  L  M  D  L  K  W  T  F  L  V  S  L  A  L  Y  L  I  G  S  L  I  C  G  V
```

FIG. 2a

```
gLE6   GCAAACTCTTCTGAGCTTCATTTTTGCCGATCGATTGCAGGAGTTGGCAACGCTGGCCGTCTTCCGCTGGCGTG    1725
cLE6   GCAAACTCTTCTGAGCTTCATTTTTGCCGATCGATTGCAGGAGTTGGCAACGCTGGCCGTCTTCCGCTGGCGTG
       A  N  S  S  E  L  L  I  F  G  R  S  I  A  G  V  G  N  A  G  V  F  A  G  V gLE6   TTCATCATTATTGCTCGAAACGTTCCTCTGCGGAAACGCCACTTTATGCTGGATTGGTTGGAGCGACTTTGCCAT    1800
cLE6   TTCATCATTATTGCTCGAAACGTTCCTCTGCGGAAACGCCACTTTATGCTGGATTGGTTGGAGCGACTTTGCCAT
       F  I  I  A  R  N  V  P  L  R  K  R  T  L  C  W  I  G  W  S  D  F  G  N gLE6   TGCTGCTGTGCTGACCTGTCCTGGGTGGTATCTTTACTGACCGTATTAGCTGGAGGTGTGTTTGTACAGTAAG    1875
cLE6   TGCTGCTGTGCTGACCTGTCCTGGGTGGTATCTTTACTGACCGTATTAGCTGGAGGTGTGTTTGTACA[-----
       C  C  C  A  G  P  V  L  G  G  I  F  T  D  R  I  S  W  R  W  C  L  Y  I gLE6   TCTCTAGAACCCGTGCACTTTATTCCGTTCATTGACACTTTCAACAGTTAACCTGCCTATCGGAGCTGTACGTG    1950
cLE6   --------INTRON A--------------------------------------]TTAACCTGCCTATCGGAGCTGTACGTG
                                                                 N  L  P  I  G  A  V  R  V gLE6   TCGCAATCATCATATATTCCTCCTTCCATCTCGTCCTGGCCGAAAAGGCAGAAGTCAAGGACCTGTCCTGGTGGC    2025
cLE6   TCGCAATCATCATATATTCCTCCTTCCATCTCGTCCTGGCCGAAAAGGCAGAAGTCAAGGACCTGTCCTGGTGGC
       A  I  I  F  L  L  P  S  R  P  G  E  K  A  A  E  V  K  D  L  S  W  W  Q gLE6   AGTTCTTCCTAAAGCTCAATCCTTTTGGGTCGGGCTCTCCTACTCGGTTCCCTGACGTGCTTTTTCCTCGCCTAC    2100
cLE6   AGTTCTTCCTAAAGCTCAATCCTTTTGGGTCGGGCTCTCCTACTCGGTTCCCTGACGTGCTTTTTCCTCGCCTAC
       F  F  L  K  L  N  P  F  G  S  A  L  L  G  S  L  T  C  F  F  L  A  L  Q gLE6   AGTGGGGCGGGCGAATACCGTTGGAGTGCTGTCGTTGCTGTACTGGTCGTGTTGCCCGTCAGCTTCA    2175
cLE6   AGTGGGGCGGGCGAATACCGTTGGAGTGCTGTCGTTGCTGTACTGGTCGTGTTGCCCGTCAGCTTCA
       W  G  G  E  Y  R  W  S  A  G  R  V  V  A  V  L  V  V  F  A  V  S  F  I
```

FIG. 2b

```
gLE6  TCGGATGGCTGGTTCTGCAATACTTCCAAGGCGACGAAGCCACACTGCCATTTAACGTTGCAAAACAGCGTACCG  2250
cLE6  TCGGATGGCTGGTTCTGCAATACTTCCAAGGCGACGAAGCCACACTGCCATTTAACGTTGCAAAACAGCGTACCG
       G  W  L  V  L  Q  Y  F  Q  G  D  E  A  T  L  P  F  N  V  A  K  Q  R  T  V gLE6  TTGGTGGTGCCTCTATCTACACTCTGCATCTGAGCGCCGCATTTGGACTCGTCATATACTATCTGCCTCTCTGGT  2325
cLE6  TTGGTGGTGCCTCTATCTACACTCTGCATCTGAGCGCCGCATTTGGACTCGTCATATACTATCTGCCTCTCTG[-
       G  G  A  S  I  Y  T  L  H  L  S  A  A  F  G  L  V  I  Y  Y  L  P  L  W gLE6  GAGTTGATTCATGAGCATGCACTGGGCTCACGAACTGACATTATGAAGGTTTCAAGCAGTACGATCTGACAGTGC  2400
cLE6  ------INTRON B-------------------------------]GTTTCAAGCAGTACGATCTGACAGTGC
                                                     F  Q  A  V  R  S  D  S  A gLE6  CGAAGCTGCTGCTCTCAAGCAACTTGGCATCTCGCTCATCTCGTCATTGCAGCTGGCGGTGCTGT  2475
cLE6  CGAAGCTGCTGCTCTCAAGCAACTTGGCATCTCGCTCATCTCGTCATTGCAGCTGGCGGTGCTGT
       E  A  G  L  K  Q  L  G  I  V  I  S  L  T  L  S  S  I  A  G  G  A  V gLE6  TGTAAAATAGGATATTACTATCCTTTCATTTACGCCGGAACGGTCTTATGCAGCATCGGCTCTGGCTTGCTTTA  2550
cLE6  TGTAAAATAGGATATTACTATCCTTTCATTTACGCCGGAACGGTCTTATGCAGCATCGGCTCTGGCTTGCTTTA
       V  K  I  G  Y  Y  Y  P  F  I  Y  A  G  T  V  L  C  S  I  G  S  G  L  L  Y gLE6  CACGATCACACTCGATACACCGCAATGGGATATGTAAGTAATCGAGCTCCGACTGAATTTGAACATTTCTAACGC  2625
cLE6  CACGATCACACTCGATACACCGCAATGGGATATAT[---------------- INTRON C -------
       T  I  T  L  D  T  P  Q  W  D  I gLE6  ATGACAGTATCGGTTATTCGATCGTATTCGCCATTGAATCGGCGTCAGTCTCGAGCAATCCAACGTTGCTGTCC  2700
cLE6  ------]TATCGGTTATTCGATCGTATTCGCCATTGAATCGGCGTCAGTCTCGAGCAATCCAACGTTGCTGTCC
              I  G  Y  S  I  V  F  A  I  G  I  G  V  S  L  E  Q  S  N  V  A  V  Q
```

MTSPARSTHTDTESHDVVKSDSDSESKLELEHSDSDNQDEKSNAKLAERPEA 50
KPEEDEELNDQGERYICGWPLVFLLLAMVSTVFIVALSNTIISTAIPAIT 100
TAFNSTRDIGWYNSGEALAATAFQLPFGRAYLLMDLKWTFLVSLALYLIG 150
SLICGVANSSELLIFGRSIAGVGNAGVFAGVFIIIARNVPLRKRTLCWIG 200
WSDFCHCCCAGPVLGGIFTDRISWRWCLYINLPIGAVRVAIIIFLLPSRP 250
GEKAAEVKDLSWWQFFLKLNPFGSALLGSLTCFFLALQWGGGEYRWSAG 300
RVVAVLVVFAVSFIGWLVLQYFQGDEATLPFNVAKQRTVGGASIYTLHLS 350
AAFGLVIYYLPLWFQAVRSDSAEAAGLKQLGIVISLTLSSIAAGGAVVKI 400
GYYYPFIYAGTVLCSIGSGLLYTITLDTPQWDIIGYSIVFAIGIGVSLEQ 450
SNVAVQTVLPDAQIPAGTSLVLFVRLLGSAIPGPIGQSVLQTTLASRLGT 500
EVAEQAYGGTGATEIRSKLDNIFGAGTPEARDALDAFNDSVTKIFMVAII 550
VSCLSALPLPLIELKSVKREKRDNEDAKEGKKTNGTTREIEDPEKGQSAE 600
IVGKAV 606

```
Consensus   ----______ _GP__GG___ __----__WR __FLIN_PIG ____-_____
CmcT        WSGVVGASTA AGPIIGGLLV QH----VGWE AVFFINVPVG LAALV------
MmrB        ----VSAASA LGPFIGGVLV QL----AGWQ SIFLINVPIG AAAL----IS-
TETr        --------AV LGPIVAGFLV DADLFGTGWR SVFLINLPIG VAVI----VG -
MMrS        ----VATSSG LGPIVGGLMV SA----FGWE SIFLINLPIG AICM----AM -
ToxA        ----ECVALI IGPIIGGAIA DN----IGWR WCFWINLPIG --AA-VCAIL--
SGE1        ----TVIAEG VGPFIGGAFN EK----LSWR WCFYINLPIG --AF-AFIIL--
CFP         ----FCHCCG AGPVLGGIFT DR----ISWR WCLYINLPIG --AV-RVAI---
ActVA-1     LASVASVGLV LGFLLSGVIT QL----FSWR WIFLINIPLF --QG-VER----
LmrA        ----ASVGLV LGFLLSGVIT QL----FSWR WIFLINIPLV --SL-VLVAV--
EMRB        -----IVAPI CGPILGGYIS DN----IHWG WIFFINVPIG --VA-VVLMT--
QacA        ----SSIGAV FGPIIGGALL EQ----FSWH SAFLINVPFA IIVA-VAGLF--
TcmA        -------GAS -GNILGGVFT EF----LSWR SVLLVNVPIG IPVLFLAARV--
```

FIG. 8a

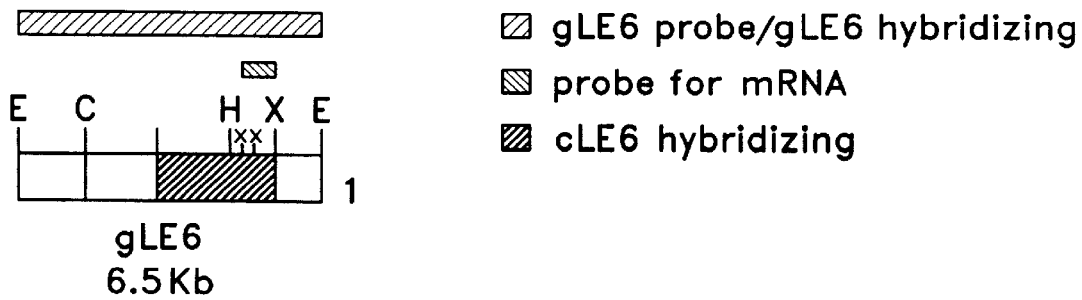
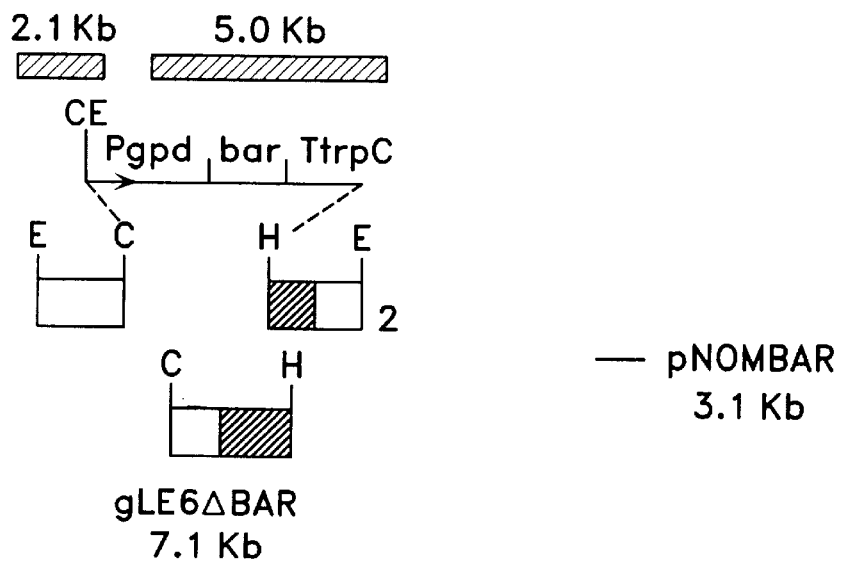
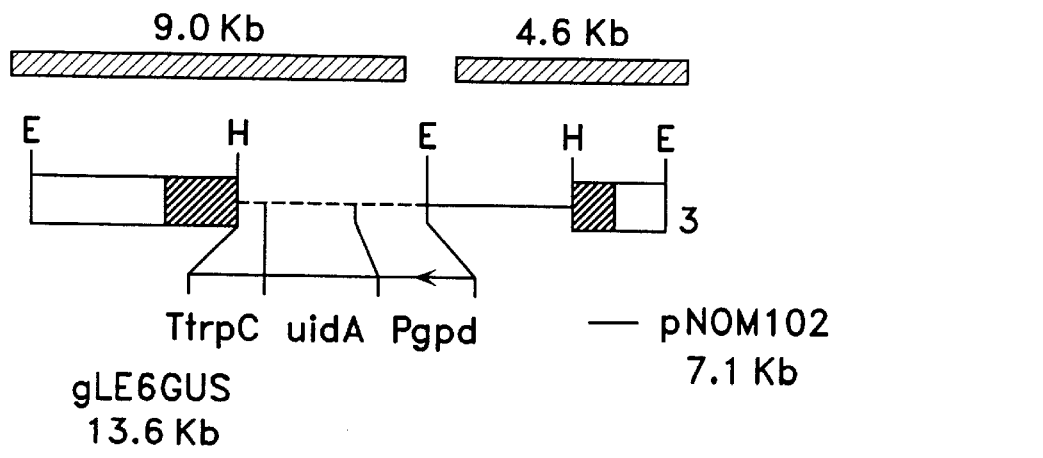
FIG. 9a

FUNGAL GENE ENCODING RESISTANCE TO THE PHYTOTOXIN CERCOSPORIN

BACKGROUND OF THE INVENTION

1. Field of the Invention

This invention relates to nucleic acid and amino acid sequences which regulate the polyketide toxin cercosporin, gene constructs, and methods related thereto. It further relates to the use of a nucleic acid to genetically engineer plants for resistance to the toxin.

2. Description of the Prior Art

Fungi of the genus Cercospora are widespread, economically important pathogens of a diverse array of crop plants, including for example, banana, sugar beet, coffee, tobacco, corn, sorghum, peanut, and soybean (Agrios, Plant Pathology, 3rd Ed., Academic Press, San Diego, Calif., 356–357, 1988). Resistance to the phytotoxin, cercosporin, produced by many species of plant pathogenic Cercospora fungi, has not been found in any commercial crops. Cercosporin is the major disease factor in purple-seed stain of soybeans and other crop diseases caused by this fungus. United States corn growers have experienced increasingly serious outbreaks of gray leaf spot disease due to *Cercospora zeae-maydis*. The lack of highly resistant plant cultivars, particularly early maturing corn in the Midwest, is crucial. With a total United States value of over $16 billion, corn growers, state economies, and commercial hybrid seed producers face potentially dramatic economic loss due to gray leaf spot. The situation with soybeans, while significant, is less dramatic. Soybean yield losses due to purple-seed stain have averaged about 1–2% or less in recent years. But the United States soybean crop is now valued at over $11 billion. The presence of more than 5% purple-stained beans at market results in significantly lower grower prices due to lower bean quality and the additional processing required for purple-stained beans. Furthermore, substantial crop losses have been attributed to the leaf phase of the disease in the southern United States when weather conditions favor the disease. One new approach to crop disease management is the use of pathogen-derived genes for resistance.

Scientists have traditionally used cross-breeding and hybridization techniques to provide plants having particular desired traits such as increased hardiness, nutritional value, taste, appearance, and disease resistance, etc., but these techniques are at best lengthy, time- consuming processes which do not necessarily result in achievement of a particular goal. With soybean, an oilseed of major importance to the world's economy, the search for enhanced or durable resistance to Cercospora is complicated by the fact that cultivar susceptibility to foliar and seed infections have no strong relationship. Indeed, some cultivars show resistance to seed stain and susceptibility to leaf blight. The advent of genetic engineering provides the opportunity to introduce genetic material directly into a plant, which upon expression in the plant, would result in a plant with resistant to cercosporin.

Polyketides such as cercosporin, for example, are products of secondary metabolism in bacteria, fungi, and plants. This group of compounds includes important bacterial and fungal antibiotics, plant flavonoids and fungal mycotoxins and phytotoxins (Hopwood et al, Annual Review of Genetics, Volume 24, 37–66, 1990). Many phytopathogenic fungi of the genus Cercospora produce the red polyketide toxin, cercosporin (Daub, Phytopathology, Volume 72, 370–374, 1982; Lynch et al, Trans. Br. Mycol. Soc., Volume 69, 496–498, 1977) which was first isolated from C. kikuchii (Kuyama et al., J. Am. Chem. Soc., Volume 79, 5725–5762, 1957). The structure of cercosporin, a red perylene quinone derivative, [1,12-bis(2-hydroxy-propyl)-2,11 dimethoxy-6, 7-methylenedioxy-4,9-dihydroxyperylene-3,10-quinone; Molecular Weight: 534] was determined independently by Lousberg et al (J. Chem. Soc. Chem. Commun., 1971:1463–1464, 1971) and Yamazaki et al (Agric. Biol. Chem., Volume 36, 1707–1718, 1972). Cercosporin is a non-host-specific toxin, which, in the presence of light, interacts with molecular oxygen to produce both superoxide radicals and singlet oxygen (Daub et al, Plant Physiol., Volume 73, 855–857, 1983). These activated oxygen species cause peroxidation of cell membrane lipids resulting in electrolytic leakage, a decrease in membrane fluidity and cell death (Daub, ACS Symp. Ser., Volume 339, 271–280, 1987). Several lines of evidence indicate that cercosporin plays an essential role in Cercospora pathogenicity: high light intensity is absolutely required for both disease development (Calpouzos, Ann. Rev. Phytopathology, Volume 4, 369–390, 1966; Calpouzos et al, Phytopathology, Volume 57, 799–800, 1967) and toxin action (Daub, 1982 supra), toxin can be isolated from naturally infected tissues (Fajola, Physiol. Plant Pathol., Volume 13, 157–164, 1978; Upchurch et al, Appl. Environ. Microbiol., Volume 57(10), 2940–2945, 1991); application of the toxin alone can produce disease symptoms on host plants (Balis et al. Phytopathology, Volume 61, 1477–1484, 1971; Fajola, 1978, supra), and non-toxin-producing mutants of Cercospora kikuchii fail to induce disease symptoms in soybean plants (Upchurch, 1991, supra). Although little is known about the biosynthesis of cercosporin, results from nuclear magnetic resonance and mass spectrometry analysis have indicated a polyketide route of synthesis and one unstable polyketomethylene intermediate has been proposed but not isolated (Okubo et al, Agric. Biol. Chem., Volume 39, 1173–1175, 1975). No enzymes or chemical intermediates in the cercosporin biosynthetic pathway have been identified. The identification and isolation of a gene responsible for conferring a major level of resistance to cercosporin-producing microorganisms would allow the development of crops resistant to fungal diseases caused by this toxin. Although there are no reports of resistance to cercosporin in crop plants, Batchvarova et al (Phytopathol., Volume 82, 1477–1484, 1992) disclose a cercosporin resistance in a common weed. The annual weed, Louisiana red rice is resistant to all known races of *Cercospora oryzae* and has a resistant to cercosporin. In sensitive rice plants, cercosporin was demonstrated to accumulate in plant tissue, a phenomenon which has been seen in soybean. It was hypothesized that the resistance seen in Louisiana red rice is due to a combined effect of active efflux of the toxin from resistant cells possibly associated with cercosporin degradation or the action of carotenoids in quenching active oxygen species. U.S. Pat. No. 5,262,306 (Robeson et al) discloses cercosporin-resistant bacteria that have the ability to degrade cercosporin. The patent also states that the gene responsible for this cercosporin-degrading characteristic could be isolated and cloned in an appropriate vector and inserted into a plant.

Cercosporin-resistant crop plants have not been discovered to date. Therefore, the development of transgenic cercosporin-resistant plant varieties would be a useful approach to the control of Cercospora-induced plant diseases. The present invention, described below, provides a direct means to genetically engineer plants with resistance to this universally toxic polyketide, cercosporin, which is different from the prior art.

SUMMARY OF THE INVENTION

It is therefore an object of the present invention to provide DNA capable of conferring cercosporin resistance to plants.

A further object of the invention is to provide DNA for the expression of the Cercospora kikuchii cercosporin membrane pump protein.

Another object of the present invention is to provide a protein capable of conferring cercosporin resistance to plants.

A still further object of the invention is to provide a protein which is a cercosporin membrane pump protein.

A further object of the present invention is to provide a cercosporin resistant hybrid plant that produces progeny with cercosporin resistance.

Another object of the present invention is to provide a vector containing a DNA sequence capable of conferring cercosporin resistance to plants.

A still further object of the present invention is to provide a vector containing a DNA sequence for the expression of a protein which is a cercosporin membrane pump protein.

Another object of the present invention is to provide a transformed prokaryote containing a vector with a DNA sequence for the expression of a cercosporin membrane pump protein.

A further object of the present invention is to provide a method for conferring cercosporin resistance to plants using a plant transformation vector containing a DNA sequence for the expression of a cercosporin membrane pump protein.

Further objects and advantages of the present invention will become apparent from the following description.

Deposit of Microorganisms

The LE6(cfp) cDNA of the present invention known as plasmid cLE6-cfp was deposited in accordance with the provisions of the Budapest Treaty with the American Type Culture Collection, 12301 Parklawn Drive, Rockville, Md. 20852 on Mar. 15, 1996. The Accession Number is ATCC 97482.

BRIEF DESCRIPTION OF THE DRAWINGS

FIGS. 2a–2d show the genomic DNA sequence, cDNA sequence and the amino acid sequence for LE6-cfp.

FIG. 3 is an amino acid sequence for LE6-cfp showing a MacVector generated translation of the Open Reading Frame. Double underlined amino acid sequences are hydrophobic, alpha helical transmembrane regions as determined by Tmpred-Prediction of Transmembrane Regions and Orientations. Lower-case, bold letters represent the 19 amino acids comprising the motif associated with all known efflux drug resistance transporters.

FIG. 4 shows a comparative amino acid homology of the region surrounding the 19 amino acid motif as generated by a search of the BLAST peptide sequence databases. CmcT=cephamycin export protein from *Norcardia lactamdurans;* MmrB=methylenomycin resistance protein from *Streptomyces coelicolor;* TETr=tetracycline resistance protein from Aeromonas; MMrS=another methylenomycin resistance protein identical to MMrB; ToxA, HC=toxin resistance protein form *Cochliobolus carbonum;* SGE1=crystal violet resistance protein from *Saccharomyces cerevisiae;* CFP=cercosporin facilitator protein (the protein of the instant invention); ActVA-1, ORF-1=transmembrane protein of actinorhodin gene cluster from Streptomyces coelicolor; LmrA=lincomycin resistance protein from *Escherichia coli;* QacA=antiseptic resistance protein from Staphylococcus aureus; TcmA=tetracenomycin resistance protein from *Streptomyces glaucescens*.

Figure 8A:
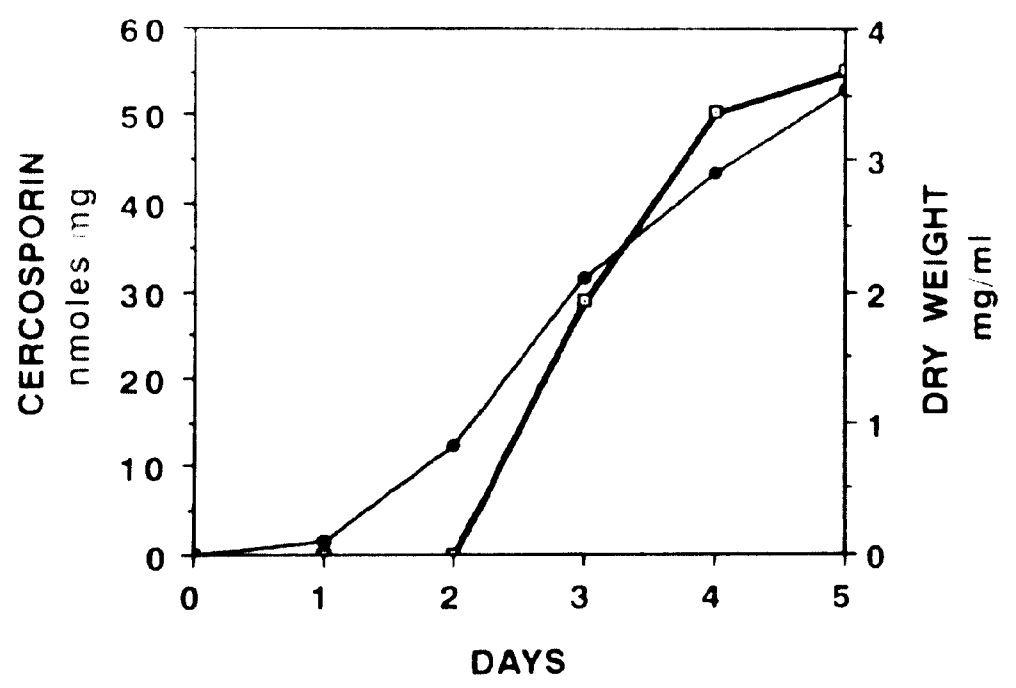

FIG. 8a is a graph showing time-course analysis of dry weight, cercosporin accumulation, and steady-state levels of RNA corresponding to the light-enhanced cDNAs cLE6 and cLE7 in wild-type strain PR.

FIG. 8b is a autoradiograph showing slot blot analysis of total RNA extracted from the samples used to generate the results shown in FIG. 7a.

FIG. 9a depicts two different disrupted versions of the LE6 protein constructed and transformed in *C. kikuchii* PR as well as genomic LE6 (gLE6).

DETAILED DESCRIPTION OF THE INVENTION

The isolation and cloning of a cDNA and its genomic DNA which is involved in cercosporin regulation according to the present invention enables the production of cercosporin-resistant plant varieties and cercosporin-susceptible Cercospora strains. Cercosporin allows the fungus to colonize and extract nutrients for growth and sporulation in infected plant tissues. Environmental conditions such as light intensity, temperature and nutrient relationships affect cercosporin production in culture. While temperature and growth medium composition affect the quantity of toxin produced, light appears to be the dominant regulatory cue (Jenns et al, Phytopathology, Volume 79, 213–219, 1989; Lynch et al, Trans. Br. Mycol. Soc., Volume 73, 311–327, 1979; all herein incorporated by reference). This means that light should regulate certain genes that are involved in cercosporin metabolism.

Figure 1:
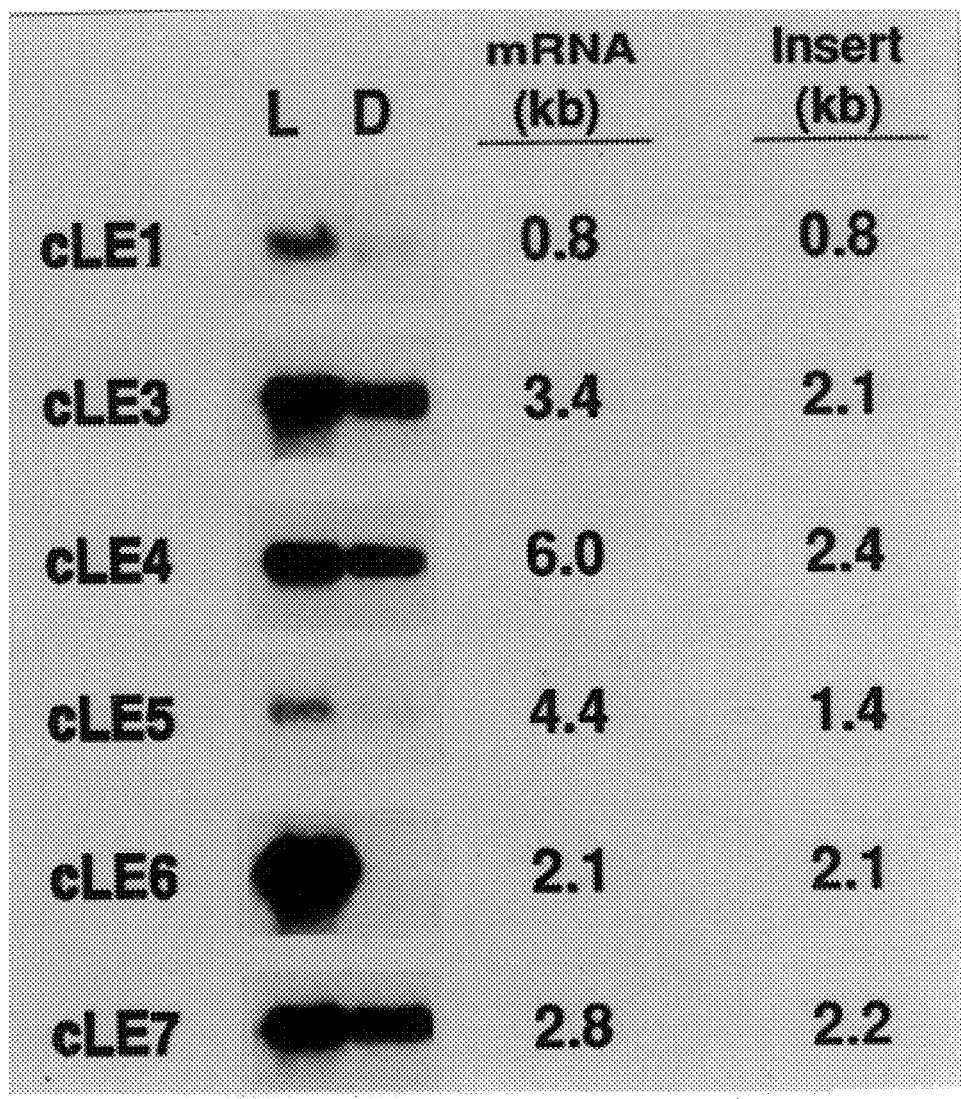
FIG. 1 is a Northern hybridization analysis of wild-type *C. kikuchii* PR. Two micrograms of poly-A$^+$RNA from light(L)- and dark(D)-grown PD broth cultures per lane was electrophoresed through a denaturing 1.2% agarose gel and transferred to nitrocellulose. Duplicate blots were probed with $^{32}$P-labeled insert DNA from each of the cLEs (cLE1 and cLE3 and cLE7).
Figures 2, 2A:
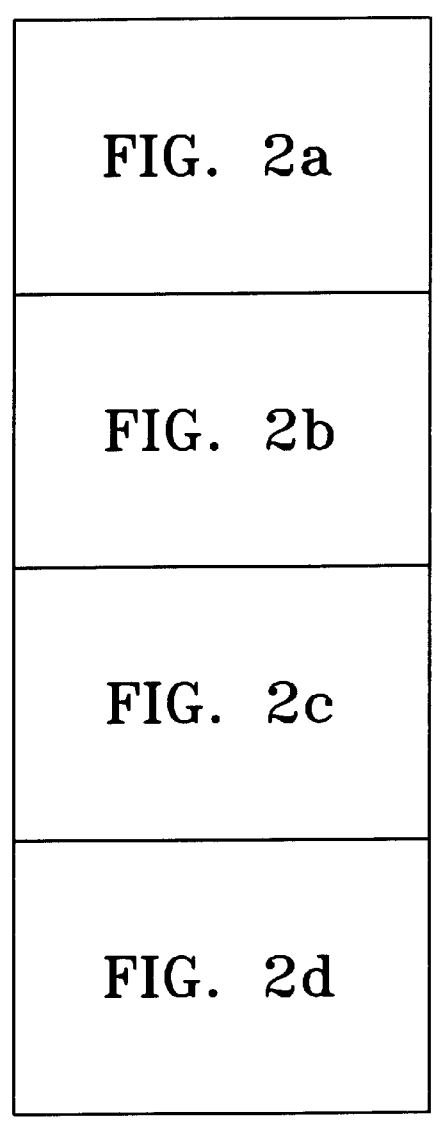
Figure 2D:
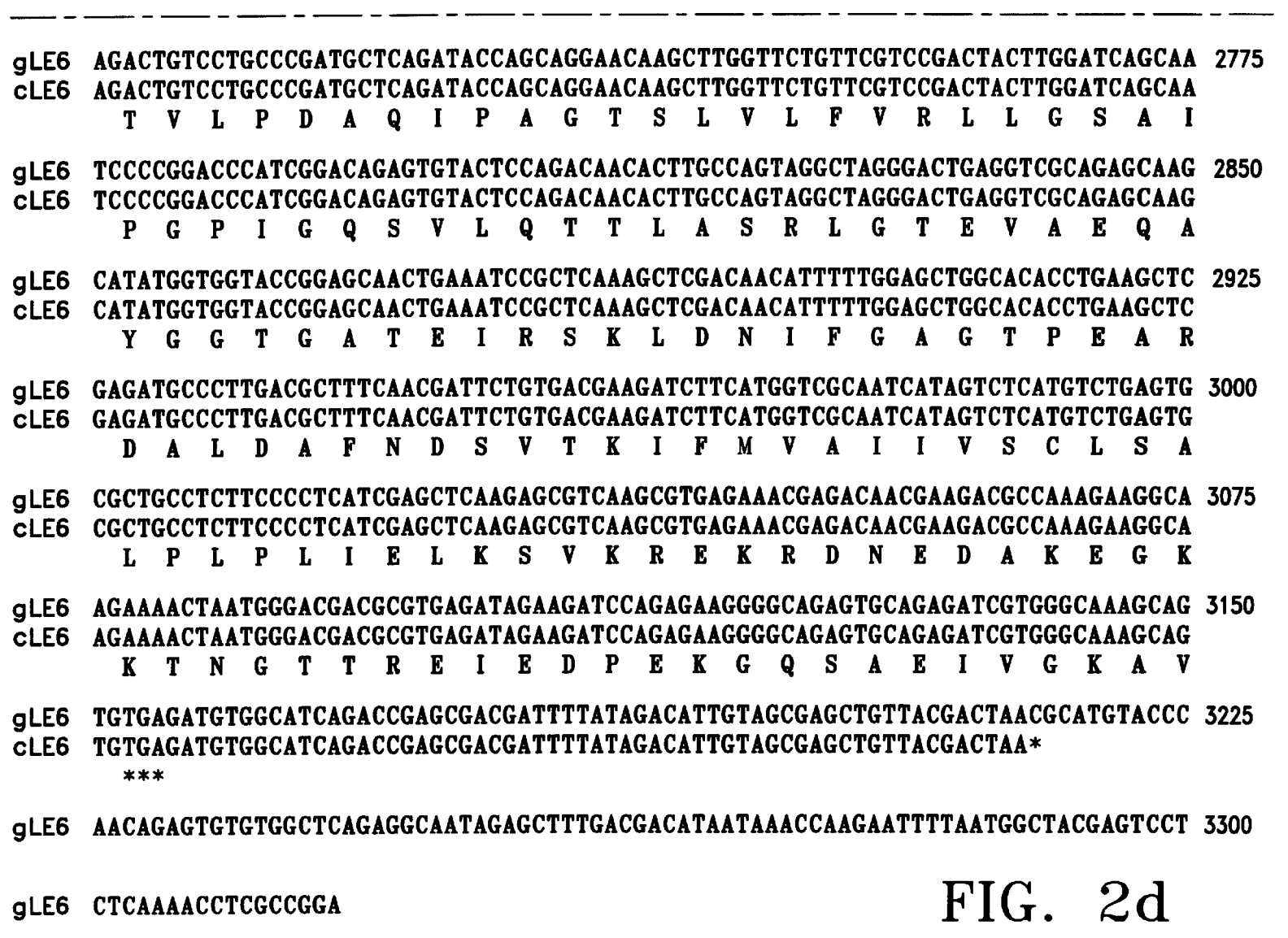
Figure 5:
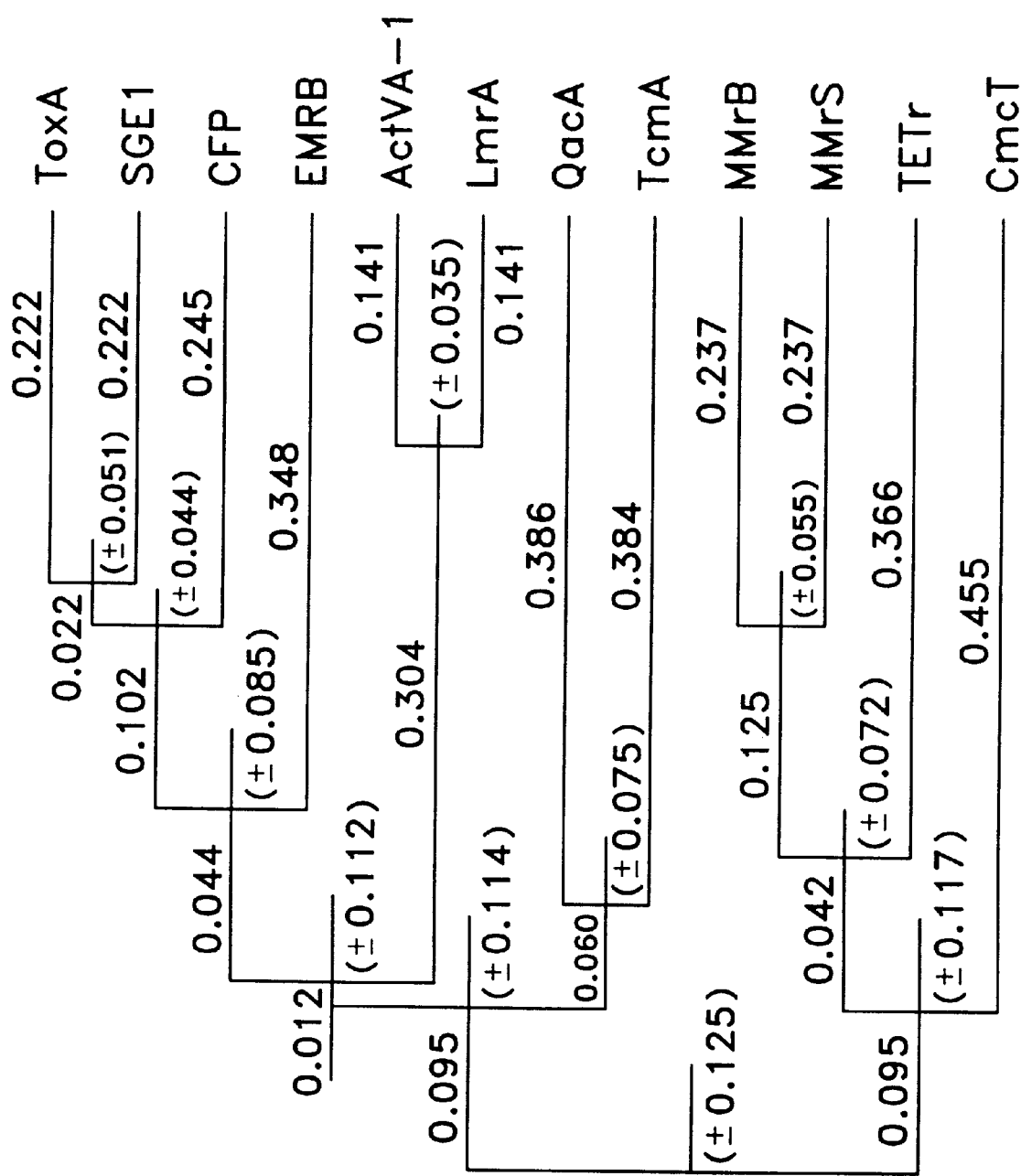
FIG. 5 shows a phylogenetic tree showing the relative relatedness among the LE6 protein and other drug transport proteins.
Figure 6:
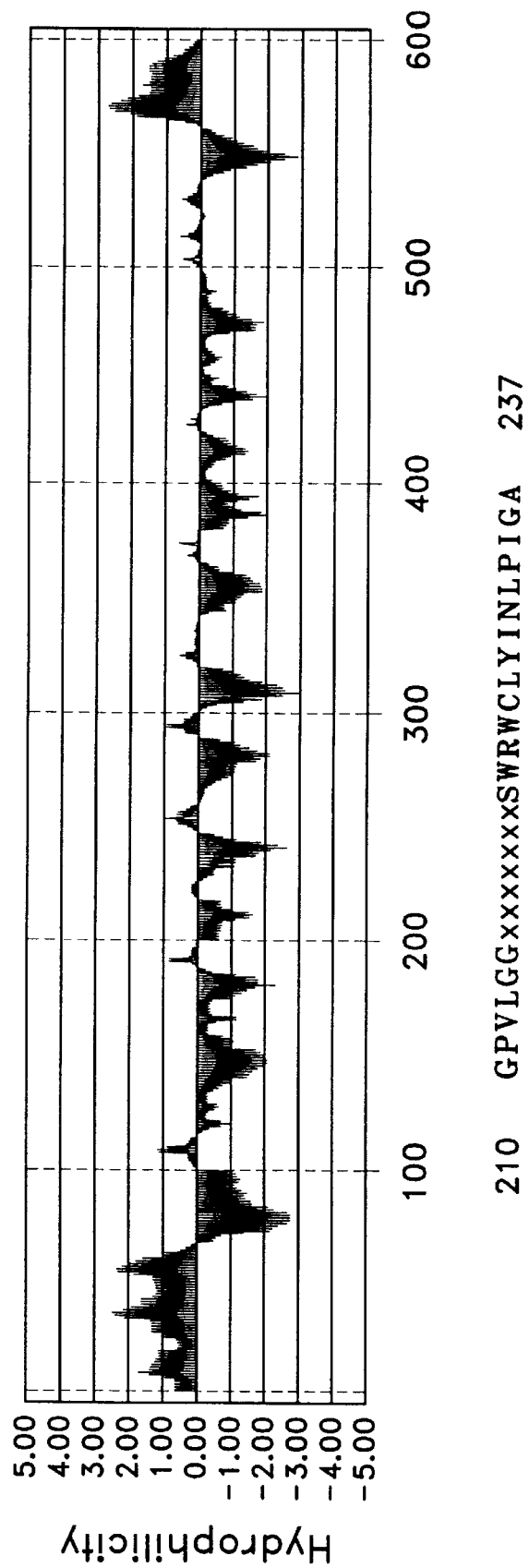
FIG. 6 is a MacVector hydrophilicity plot of the LE6 protein showing the position of the 19 amino acid motif relative to the entire sequence.

Light induction was used to isolate light-enhanced cDNAs by a subtractive hybridization technique (Maniatis et al, Molecular Cloning: A Laboratory Manual, pages 8.49 and 10.40–10.43, 1989; herein incorporated by reference). A cDNA library was constructed with the bacteriophage lambda vector lambda-ZAPII (Stratogene Cloning Systems, La Jolla, Calif.) by using poly-A⁺ RNA isolated from light-grown, wild type *Cercospora kikuchii* PR. The library is maintained as a bacteriophage stock and infected into *Escherichia coil* XL1-blue cells (Stratogene Cloning Systems, La Jolla, Calif.) for screening. To isolate light-regulated cDNAs from this library, a subtracted probe is made from light-grown *C. kikuchii* poly-A⁺ RNA and used to probe high-density plaque lifts. Single hybridizing plaques are isolated and converted into plasmids using a helper bacteriophage and an in vivo plasmid excision technique (Stratogene). Inserts from these plasmids are then used to probe Northern (RNA) blots containing poly-A⁺ RNA from light- and dark-grown *C. kikuchii* cultures. Six light-enhanced cDNA clones, cLEs, each of which hybridize to a single distinct mRNA band on Northern blots, are identified (FIG. 1). One of these cDNAs, LE6, shows enhanced transcript accumulation 20-fold higher in light and is correlated with the accumulation of cercosporin in culture and is nearly full length at 2.1 kb. The sequence of this cDNA (FIG. 2) contains a putative open reading frame (ORF) of 1,818 base pairs that encodes a predominantly hydrophobic, cysteine-rich protein of 606 amino acids (pLE6) (FIG. 2) with a molecular weight of 65,424 and an isoelectric point of 5.08. MacVector generated translation of the ORF shows sequences that are hydrophobic, alpha helical transmembrane regions, as determined by the Tmpred-Prediction of Transmembrane Regions and Orientation as seen in FIG. 3 (Hofmann et al, Chem. Hoppe-Seyler, Volume 347, 166–176, 1993). Kyte-Doolittle analysis of the protein indicates the pLE6 contains 12–13 transmembrane alpha helical regions. An amino acid sequence homology search has identified two regions of homology, GPVLGG and SWRWCLYINLPIG, to efflux-mediated resistance determinants, a subfamily of the major facilitator superfamily (FIG. 4). A comparative amino acid homology of the region surrounding this 19 amino acid motif was generated by a search of the BLAST peptide sequence databases (FIG. 4). Homology was found in the following efflux drug resistance transporters: CmcT, cephamycin export protein from *Nocardia lactamdurans* (Coque et al, EMBO J., Volume 12, 631–639, 1993); MmrB, methylenomycin resistance protein form *Streptomyces coelicolor* (Neal et al, Gene, Volume 58, 229–241, 1987); TETr, tetracycline resistance protein from Aeromonas (Varela et al, Antimicrob. Agents Chemother., Volume 37, 1253–1258, 1993); MmrS, another methylenomycin resistance protein identical to MMrV; ToxA, HC toxin transport protein form *Cochliobolus carbonum* (J. Pitkin, Michigan State University, personal communication); SGE1, crystal violet resistance protein from *Saccharomyces cereviseae* (Eherhofer-Murray et al, Mol. Gen. Genet., Volume 244, 287–294, 1994); CFP (LE6), cercosporin facilitator protein; ActVA-1, ORF-1, transmembrane protein of the actinorhodin gene cluster from *Streptomyces coelicolor* (Cavallero et al, Mol. Gen. Genet., Volume 230, 401–412, 1991); LmrA, lincomycin resistance protein from *Streptomyces lincolnensis* (Zhang et al, Molec. Microbiol., Volume 6, 2147–2157, 1992); EMRB, multidrug resistance protein from *Escherichia coli* (Lomovskaya et al, Proc. Natl. Acad. Sci., USA, Volume 89, 8938–8942, 1992); QacA, antiseptic resistance protein from Staphylococcus aureus (Tennent et al, J. Gen. Microbiol., Volume 135, 1–10, 1989); and TcmA, tetracenomycin resistance protein from *Streptomyces glaucescens* (Guilfoile et al, J. Bacteriol., Volume 174, 3651–3658, 1992). FIG. 5 depicts a phylogenetic tree showing the relative relatedness among pLE6 and other drug transport proteins. The tree was constructed using the Unweighted Pair Group Method supplied by GeneWorks nucleic acid/protein analysis software (IntelliGenetics Inc., Mountain View, Calif.). A MacVector hydrophilicity (inverse of hydropothy) plot indicates the position of the 19 amino acid motif relative to the entire sequence as being between amino acid 210 to amino acid 237 as shown in FIG. 6. These data suggest that LE6 is responsible for the movement of cercosporin across the plasma membrane. Further analysis shows that this hydrophobic protein contains a region with significant amino acid sequence homology to both prokaryotic and yeast proteins involved in antibiotic resistance. Genomic Southern analysis shows that LE6cfp exists in the genomes of other phytopathogenic Cercospora species such as, for example, *Cercospora beticola* (Sugar beet), *Cercospora nicotianae* (tobacco), and *Cercospora zeae-maydis* (corn).

Gene disruption of LE6 results in dramatically reduced cercosporin production in *C. kikuchii* grown in continuous light, loss of *C. kikuchii* pathogenicity on soybean, diminished transcript accumulation of another light-enhanced cDNA, an altered pigment accumulation profile, and substantial loss of auto-resistance to cercosporin.

Figure 7:
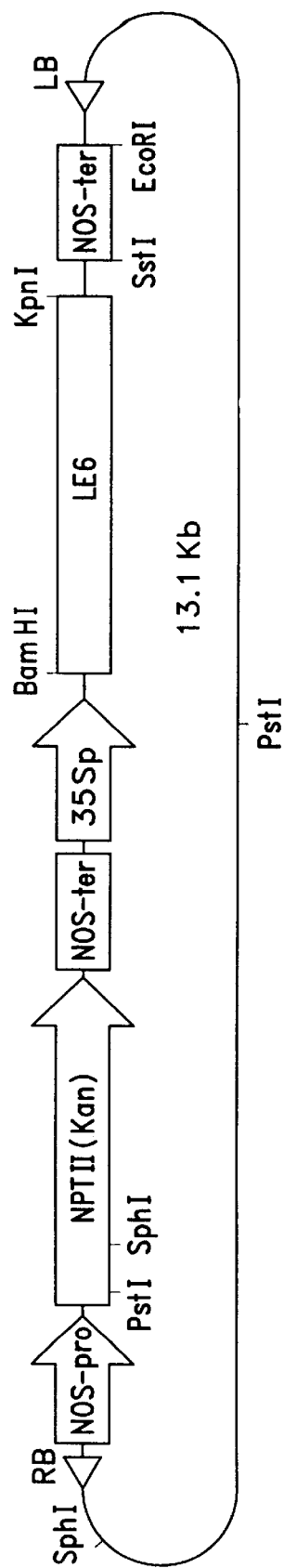
FIG. 7 depicts plant expression vector pB35S-LE6CFP which includes a 2.1 kb BamHI/KpnI fragment comprising the entire length of LE6-cfp cDNA.
Figure 8B:
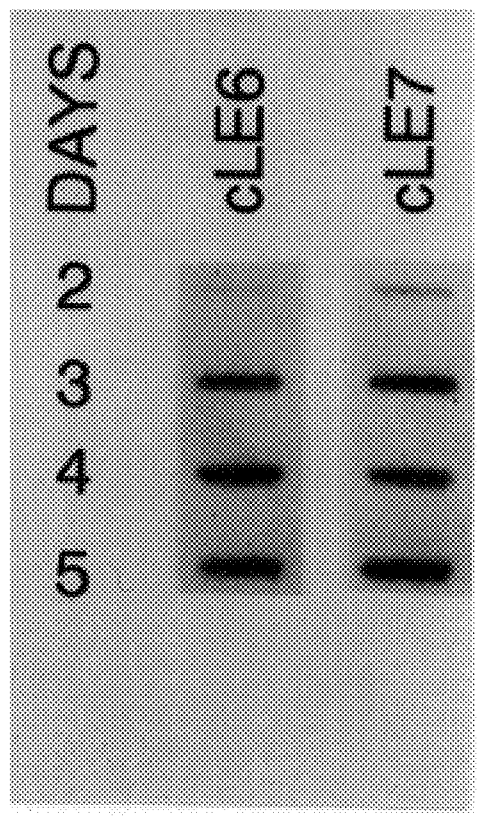

All this evidence indicates that pLE6 is responsible for moving cercosporin across the plasma membrane, i.e. that it is a membrane pump, to confer fungal resistance. This further indicates that it can be inserted into plant cells to make transgenic plants which are resistant to cercosporin. A cercosporin resistant transgenic plant is any transgenic plant that exhibits any level of cercosporin resistance as compared to the nontransformed plant. The DNA construct can be introduced into a plant using any method which provides for efficient transformation. Various methods for plant transformation include the use of Ti- or Ri-plasmids, DNA particle bombardment, micro injection, electroporation, liposome fusion, DNA bombardment, etc. See for example, Gordon-Kamm et all, The Plant Cell, Volume 2, 603–618, 1990; and Lowe et al, BIO/TECHNOLOGY, Volume 13, 677–682, 1995; all herein incorporated by reference. The plant tissue is genetically engineered with cDNA (LE6cfp) isolated from *Cercospora kikuchii* PR (*C. kikuchii* PR) and put into a plant expression vector such as, for example, pBIN/35S (Bevan, Nuc. Acids Res., Volume 12, 8711–8721. A 2.1 kb BamHI/KpnI fragment comprising the entire length of LE6(cfp) cDNA (FIG. 2) was cloned into the polylinker site of the plant expression vector pBIN/35S as described by Bevan (supra) (FIG. 7).

The following examples are intended only to further illustrate the invention and are not intended to limit the scope of the invention as described by the claims.

EXAMPLE 1

*Cercospora kikuchii* PR was isolated from soybeans in Puerto Rico and was provided by J. B. Siclair, University of Illinois, Urbana, Ill. Fungi are grown on potato dextraose medium (Difco Laboratories, Detroit, Mich.) in either liquid (PD) or agar-solidified (PDA) forms. Fungi cultured in liquid medium are grown in 50-ml volumes in 125-ml Erlenmeyer flasks on a rotary shaker (180 rpm) at 20° C. under continuous white fluorescent light (approximately 15 microeinsteins $m^{-2}$ $s^{-1}$ or continuous dark.

EXAMPLE 2

In order to isolate light-induced cDNAs, cultures of *C. kikuchii* PR are grown in either continuous white fluorescent light of approximately 15 microeinsteins $m^{-2} s^{-1}$ or continuous darkness either in potato dextrose (ED) broth (Difco Laboratories, Detroit, Mich.) or complete medium (CM) containing salts, yeast extract, and casamino acids (Jenns et al, supra). The cultures are grown in shake culture (200 rpm) until early stationary phase. Five milliliter aliquots of culture (mycelium plus medium) are blended for 30 seconds in a Waring blender with 5 ml of distilled water. The resulting slurry is used to determine cercosporin concentration as described by Jenns et al (Phytopathology, Volume 79, 213–219, 1989; supra). Dry weights are determined after lyophilization.

EXAMPLE 3

In order to extract RNA and construct a cDNA library, mycelia are harvested from the liquid cultures, described in Example 2 above, by vacuum filtration through Miracloth, frozen in liquid nitrogen, and lyophilized. Lyophilized tissue is refrozen in liquid nitrogen and ground to a powder in a mortar and pestle prechilled with liquid nitrogen. Total RNA is extracted as described in Williamson et al (Plant Physiol., Volume 88, 1002–1007, 1988; herein incorporated by reference). Poly(A)$^+$ RNA is extracted from total RNA by oligo(dT) cellulose chromatography as described by Maniatis et al (supra, pages 8.49 and 10.40–10.43; herein incorporated by reference). RNA extracted from light-grown cultures, described in Example 1, is used to construct a cDNA library with the bacteriophage lambda vector lambda ZAPII (Stratagene) by using poly(A)$^+$ RNA isolated from the light-grown C. kikuchii PR. It is maintained as a bacteriophage stock and infected into Escherichia coli XL1 blue cells (Stratagene) for screening.

EXAMPLE 4

To obtain cDNA clones from the cDNA library constructed from light-grown C. kikuchii poly(A)$^+$, a subtractive hybridization technique is used as described by Maniatis et al (pages 8.49 and 10.40–10.43, supra). First-strand cDNA is synthesized from light-grown C. kikuchii poly(A)$^+$ RNA by using [$\alpha$-$^{32}$P]dCTP. Dark-grown C. kikuchii poly(A)$^+$ RNA is biotinylated and hybridized to the first-strand light-enhanced cDNA and hybrids and nonhybridized dark-grown C kikuchii poly$(A)^+$ RNA are subtracted from the mixture with strepavidin as described by Sive et al (Nucleic Acids Res., Volume 16, 10937, 1988; herein incorporated by reference). The procedure is repeated twice. After two rounds of subtraction, the remaining light-enhanced cDNA is labeled with [$\alpha$-$^{32}$P]dCT? by random hexamer priming as described by Feinberg et al (Anal. Biochem., Volume 132, 6–13, 1983; herein incorporated by reference) and this is used to probe duplicate plaque lifts, as described by Maniatis et al (pages 10.40–10.43, supra), containing the light-enhanced cDNA library. Hybridizing areas containing multiple plaques are subsequently plaque purified and the cloned DNA is converted into plasmid DNA by using a helper bacteriophage (Stratagene) and an in vivo plasmid excision technique (Stratagene, herein incorporated by reference).

EXAMPLE 5

To isolate specific clones for which corresponding mRNAs exhibit enhanced accumulation in the light, 2 ig samples of glyoxylated poly$(A)^+$ RNA are electrophoresed under denaturing conditions through a 1.2% agarose gel as described by Maniatis et al (supra) and transferred to nitrocellulose. For slot blot analysis, either 10- or 20-$\mu$g samples are applied to nitrocellulose with a Schleicher & Schuell Minifold II. Hybridizations are performed in a 50% formamide buffer at 42° C. with insert DNA from the plasmids described above in Example 4 labeled to a high specific activity with [$\alpha$-$^{32}$P]dCTP by random hexamer labeling as described by Feinberg et al (supra). The probe is removed from the slot blots after hybridization by washing in 0.1× SSC (1× SSC is 0.15 M NaCl plus 0.015 M sodium citrate)-0.1 % sodium dodecyl sulfate at 95° C. The blots are then hybridized with a *Neurospora crassa* probe consisting of rDNA (genes coding for rRNA) as described by Russell et al (Mol. Gen. Gent., Volume 196, 275–282, 1984; herein incorporated by reference). Theses control hybridizations verify that all the samples within a slot blot are equally loaded. To quantitate intensity of slot blot hybridization, the autoradiographs are analyzed by laser scanning densitometry.

Six light-enhanced cDNA clones (cLEs), cLE1and cLE3–cLE7, each of which hybridize to a single distinct mRNA band on Northern blots, were identified (FIG. 1). The lengths of these transcripts range from approximately 0.8 to 6.0 kb, while the lengths of the cDNA inserts range from approximately 0.8 to 2.4 kb. Two of the cDNA clones are nearly full length, while the others range from approximately 32 to 79% of the lengths of their respective mRNAs. No transcripts for cLE6 are detected in dark-grown *C. kikuchii* poly$(A)^+$ RNA. MRNAs for the other light-enhanced sequences are detected at various levels in the dark-grown *C. kikuchii poly(A)*$^+$ RNA. These six cloned DNAs are converted into plasmid DNA by using a helper bacteriophage and an in vivo plasmid excision technique (Stratogene,supra) to form plasmid pcLE1 and pcLE3–pcLE7, especially cLE6-CFP, which are then infected into *Escherichia coli* XL1 Blue (Stratagene) cells to maintain.

EXAMPLE 6

To determine the relationship between toxin synthesis and expression of the light-enhanced cDNAs in *C. kikuchii* PR, the kinetics of transcript and toxin accumulation are compared. Samples are collected at 24 hour intervals from a single large PD broth culture. Aliquots are used for toxin analysis as described by Jenns et al (supra), and the remaining culture is recovered and lyophilized for dry weight determination and RNA extraction. Transcript accumulation is assessed by slot blot analysis of total RNA from all samples except the day one sample, which yielded too little tissue for RNA extraction. Signal intensities are quantitated by laser scanning densitometry.

The onset of toxin accumulation occurs dramatically between days 2 and 3, lagging behind the onset of logarithmic growth by at least about 24 hours (FIG. 8*a*). Transcripts for both cLE6 and cLE7 exhibit accumulation kinetics identical to that of the toxin (FIG. 8*b*); i.e., each also increased dramatically between days 2 and 3. Between days 2 and 3, cercosporin levels increased from undetectable to approximately 29 nmol/mg of fungal tissue (dry weight), while steady-state RNA levels for cLE6 and cLE7 increased approximately 16- and 4-fold, respectively. Transcripts for the other cLEs are already present at higher levels than those for cLE6 and cLE7 on day 2. They did not, however, show any marked change in steady-state level during the course of the experiment (data not shown).

Of the six cLEs, cLE6 exhibits the most striking relationship to cercosporin production. In PR, accumulation of cLE6 transcripts in the light is increased by approximately 20-fold over transcript accumulation in the dark.

EXAMPLE 7

Fungal transformations were conducted as described by Upchurch et al (Applied and Environmental Microbiology, Volume 60 (12), 4592–45951994; herein incorporated by reference). Transformants were grown on plates containing regeneration medium supplemented with 10 μM bialaphos. This allows for the selection of fungal colonies which have integrated a copy of the bar gene from *Streptomyces hygroscopicus* into their genome. Putative transformants were transferred to bialaphos-containing media for several generations to ensure stability of the marker.

EXAMPLE 8

The LE6cfp gene is contained within genomic clone gLE6. This 6.5 kb EcoRI genomic DNA fragment is used to construct deletion clones. The plasmid pCFP ΔBAR was constructed by deletion of a 2.5kb ClaI/HindIII fragment from gLE6 followed by ligation of the 3.1 kb ClaI/HindIII bar "expression unit" subcloned from the plasmid pNB1 (Upchurch, 1994, herein incorporated by reference). The bar gene confers resistance to the herbicide bialaphos (Straubinger et al, Fungal Genet. Newsl., Volume 39, 82–83, 1992; herein incorporated by reference). The plasmid pCFP GUS was constructed by excising the 6.5 kb EcoRI fragment from the gLE6 plasmid. The purified insert DNA was highly diluted and exposed to T4 DNA ligase allowing it to circularize in a head-to-tail orientation. Immediately following heat inactivation of the ligase the sample was restricted with HindIII, thus causing the gLE6 insert DNA to remain in the head-to-tail orientation with HindIII ends. The appropriate size head-to-tail construct was gel purified and ligated in the HindIII digested 7.1 kb plasmid pNOM102 (Roberts et al, Curr. Genet., Volume 15, 177–180, 1989; herein incorporated by reference). Transformations were performed as described above in Example 7 and transformants selected on regeneration medium amended with bialaphos. Southern analysis utilized EcoRI digested genomic DNA and radiolabeled gLE6 insert DNA as well as the bar and uidA genes to determine the number and locations of insertion events.

Figure 9B:
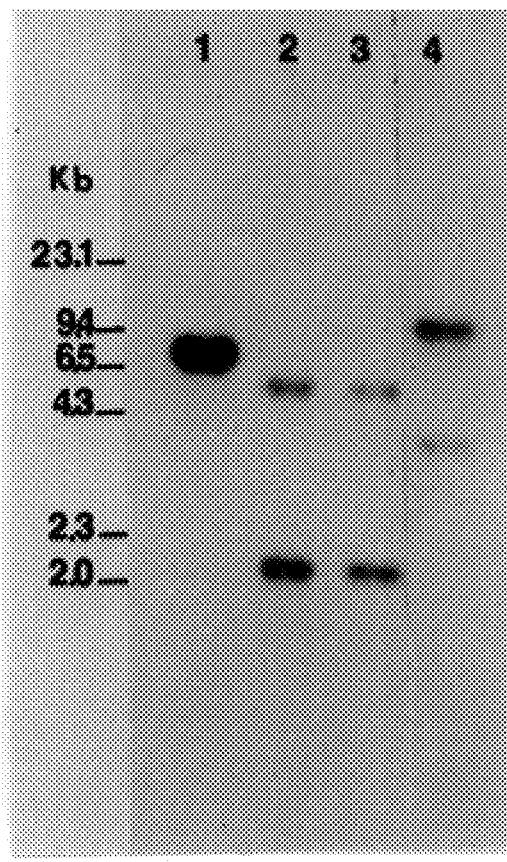
FIG. 9b shows an autoradiogram of three disruptants containing a single copy of a disrupted version of the LE6(cfp) gene. Lane 1 is wild-type strain PR, Lane 2 is Bar1, Lane 3 is Bar2 and Lane 4 is Gus3.

Two different disrupted versions of the LE6cfp gene were constructed and transformed into *C. kikuchii* PR as described above and are depicted in FIG. 9a. The number and position of insertion events was evaluated by Southern hybridization analysis of twelve bialaphos-resistant transformants of each type of disruptant. Of those colonies analyzed, three were shown to contain a single copy of a disrupted version of the LE6cfp gene (FIG. 9b). The disruptants containing pLE6CFPΔBar are denoted Bar1 and Bar2 and that containing a single copy of pLE6CFP GUS is labeled Gus3. Northern analysis was performed to assure that the disruption of the native Lecfp gene had blocked its transcription. No hybridization was shown when Bar1 and Bar2 total RNA was probed with LE6cfp, but a minimal signal was detected in steady state RNA isolated from Gus3 (data not shown).

EXAMPLE 9

Levels of cercosporin produced by disruptant transgenic *C. kikuchii* are determined by taking 10 ml aliquots of fungal liquid cultures (mycelia plus medium). The aliquots are blended in a Waring blender and treated with one volume of 5N KOH as described by Jenns et al (supra) and clarified by centrifugation. Cercosporin concentrations are determined spectrophotometrically from the $A_{480}$ and the molar extinction coefficient of 23,300 for cercosporin in base (Jenns et al, supra). Samples of lyophilized mycelia are weighed in order to express cercosporin concentration as nmol/mg dry wt.

Figure 10:
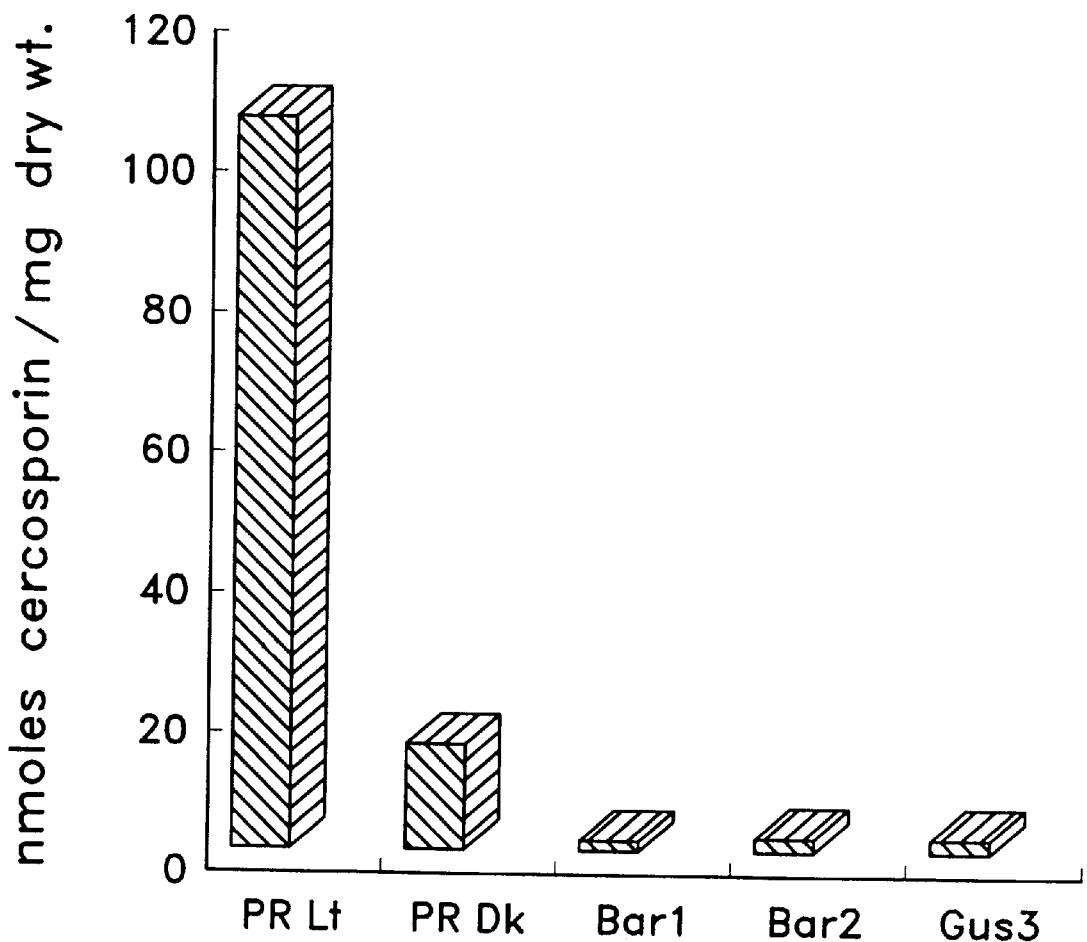
FIG. 10 is a graph showing cercosporin production by disruptant transformants Bar1, Bar2, Gus3 compared to wild-type *Cercospora kikuchii* PR grown in continuous light (PRLt) or continuous dark (PRDk).

Disruptant transformants Bar1, Bar2, and Gus3 are tan in color, rather than bright red, when grown in PD medium. The levels of cercosporin in the transformant fungi are shown FIG. 10. The levels of cercosporin production in Bar1, Bar2, and Gus3 were drastically lower than that of wild-type strain PR. Cercosporin production by Bar1 was measured at approximately 3% of wild-type, Bar2 at approximately 6%, and Gus3 accumulated approximately 5% of light-grown PR levels. The levels are significantly lower than values routinely obtained for PR cultures grown in the dark. These measurements are consistent with the levels observed by thin-layer chromatographic separation (data not shown).

EXAMPLE 10

To determine autoresistance of the transgenic fungi to cercosporin, *C. kikuchii* PR and the disruptant transformants are tested for inhibition of radial growth on agar. Fungal plugs (5 mm) are inoculated onto divided petri plates with the PDA medium on one half of each plate amended by the addition of a cercosporin stock solution to give a final concentration of 10 μM as outlined by Daub et al (Phytopathology, Volume 77, 1515–1520, 1987; herein incorporated by reference). Since the cercosporin stock is prepared in acetone, the second half of each plate is amended with an equal volume of acetone. Plates are maintained at 25° C. under continuous fluorescent light (80 microeinsteins $m^{-2}$ $s^{-1}$), and radial growth is measured 3 and 4 days after inoculation.

Figure 11:
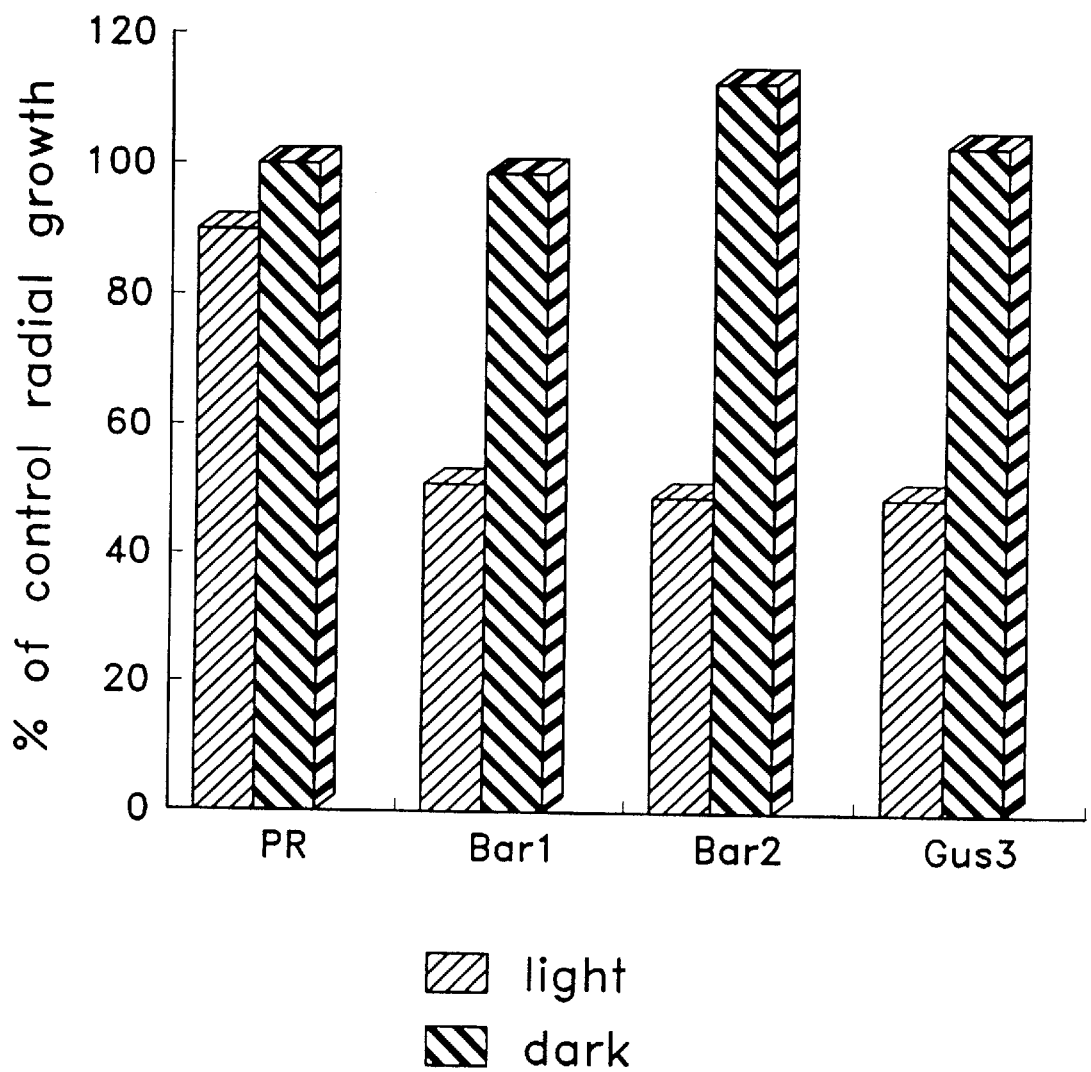
FIG. 11 is a graph showing cercosporin sensitivity of disruptant transformants Bar1, Bar2, Gus3 compared to wild-type *Cercospora kikuchii* PR. All are grown in continuous light or continuous dark and levels are shown as percent of control radial growth.

Wild-type *Cercospora kikuchii* shows only slight growth inhibition when grown in the presence of cercosporin (Daub et al, In R. Heitz et al (ed.), Light activated Pesticides, American Chemical Society, Washington, D.C., pages 271–280, 1987, herein incorporated by reference). The relative growth of wild-type and disruptant *C. kikuchii* is evaluated in the presence of cercosporin. Disruptants Bar1 and Bar2 exhibited the greatest sensitivity to cercosporin, with average percent growth inhibitions of approximately 48 and 52, respectively (FIG. 11). The other transformant, Gus3, also has average percent growth inhibition of 48. The LE6cfp disruptant strains are dramatically more sensitive to cercosporin than wild-type PR.

EXAMPLE 11

The aggressiveness of *C. kikuchii* transformants in planta is determined by leaf inoculation of greenhouse grown 5-week-old soybean (Glycine max L.) cultivar Lee-68 plants. Fungal inoculum is prepared by blending approximately 0.5 g (fresh weight) of washed, dark-grown mycelia of each strain in 20 ml of sterile water in a sterile Waring blender as described by Upchurch et al (Appl. Environ. Microbiol., Volume 57, 2940–2945, 1991, herein incorporated by reference). Mycelial suspensions are then atomized onto the underside of the leaves until inoculum runoff is acheived. Plants are covered with plastic bags for an initial 48 hour period in reduced light to maintain humidity for infection. Lesion formation is monitored over a 14-day period. Five plants are inoculated with each fungal strain tested and the entire experiment was repeated.

Thirty soybean trifoliate leaf panels (90 separate leaves) were examined in the two inoculation experiments. Irregularly shaped 2–8 mm spreading lesions with necrotic centers were observed on the upper surfaces of the Lee-68 cultivar plants 7 days after inoculation with the wild-type isolate PR.

Only pinpoint flecks were observed infrequently on leaves inoculated with the LE6 disruptant Bar1, Bar2, and Gus3 indicating the decreased aggressiveness of these mutants compared to the wild-type. No lesions were detected on plants that were mock inoculated with a water control.

This decrease in aggressiveness in the disruptant fungi appears to caused by the decrease in cercosporin production in these fungi. It has been shown that cercosporin is a critical pathogenicity factor in the infection of soybean by *C. kikuchii* (Upchurch, 1991, supra). Since the experiments show that the concentration of cercosporin produced by these fungal strains is much less than wild-type levels, it would be expected that these fungi would be less aggressive. In addition to decreased aggressiveness, these disruptant fungi may have decreased fitness in their natural environment since they have an increased sensitivity to their own toxin, although environmental fitness has not been tested.

The foregoing detailed description is for the purpose of illustration. Such detail is solely for that purpose and those skilled in the art can make variations therein without departing from the spirit and scope of the invention.

We claim:

1. A DNA sequence isolated from *Cercospora kikuchii* encoding a membrane pump protein, wherein disruption of said sequence in *Cercospora kikuchhi* causes said Cercospora to be cercosporin susceptible.

2. An isolated DNA sequence encoding a heterologous *Cercospora kikuchii* membrane pump protein, wherein disruption of said sequence in *Cercospora kikuchii* causes said Cercospora to be cercosporin susceptible.

3. A vector comprising a DNA sequence isolated from *Cercospora kikuchii* encoding a membrane pump protein, wherein disruption of said sequence in *Cercospora kikuchii* causes said Cercospora to be cercosporin susceptible.

4. A transformed cell comprising a genome which contains genetic material encoding a *Cercospora kikuchii* membrane protein pump, wherein disruption of said sequence in *Cercospora kikuchii* causes said Cercospora to be cercosporin susceptible.

5. A plant transformation vector comprising a DNA sequence isolated from *Cercospora kikuchii* encoding a membrane pump protein, wherein disruption of said sequence in *Cercospora kikuchii* causes said Cercospora to be cercosporin susceptible.

6. A transgenic plant comprising a genome which contains genetic material encoding a heterologous *Cercospora kikuchii* membrane pump protein, wherein disruption of said sequence in *Cercospora kikuchii* causes said Cercospora to be cercosporin susceptible.

7. An isolated DNA molecule comprising a sequence selected from the group consisting of
    (a) SEQ ID NO 1 and SEQ ID NO 2; and
    (b) DNA sequences which encode for a membrane pump protein having a sequence of SEQ ID NO 3.

8. A DNA construct comprising an expression cassette, said construct comprising in the 5' to 3' direction a promoter operable in a plant cell and a DNA sequence according to claim 7 positioned downstream from said promoter and operatively associated therewith.

9. The DNA construct of claim 8 carried by a plant transformation vector.

10. The DNA construct according to claim 8, wherein said promoter is the 35S promoter from Cauliflower Mosaic virus.

11. A plant cell containing a DNA construct of claim 8.

12. A transgenic plant comprising plant cells according to claim 11.

13. A method for making a transgenic plant comprising a genome which contains genetic material encoding a *Cercospora kikuchii* membrane protein pump comprising
    (a) providing a plant cell;
    (b) transforming said plant cell with an exogenous DNA construct comprising, in the 5' to 3' direction, a promoter operable in a plant cell and a DNA sequence encoding the protein of SEQ ID NO 3, said DNA sequence operatively linked to said promoter.

14. The method according to claim 13, wherein said promoter is the 35S promoter from Cauliflower Mosaic virus.

15. The method according to claim 13, wherein said transforming step is carried out by bombarding said plant cell with microparticles carrying said DNA construct.

16. A method according to claim 13, further comprising regenerating a plant from said transformed plant cell.

17. A transformed plant produced by the method of claim 13.

18. Seed or progeny of a plant according to claim 17, which seed or progeny has inherited said DNA sequence encoding a protein of SEQ ID NO 3.

19. A transformed plant produced by the method of claim 16.

20. A transgenic plant according to claim 19, wherein said promoter is the 35S promoter from Cauliflower Mosaic virus.

21. Progeny or seed of a plant according to claim 19, wherein said seed or progeny has inherited DNA sequence encoding a protein of SEQ ID NO 3.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 2192 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Cercospora kikuchii
      (B) STRAIN: PR (ix) FEATURE:
      (A) NAME/KEY: intron
      (B) LOCATION: 746..798

(ix) FEATURE:
      (A) NAME/KEY: intron
      (B) LOCATION: 1199..1248

(ix) FEATURE:
      (A) NAME/KEY: intron
      (B) LOCATION: 1459..1507

(xi) SEQUENCE DESCRIPTION: SEQ ID NO:1:

```
GCCGTCGAAT GAGTTCCCTC ATAGCAGTCT GGACCGGCTA CTTTCCATAC ATTGACAATG      60

ACGAGCCCAG CGCGATCAAC GCATACTGAT ACAGAGTCTC ACGACGTCGT AAAGAGCGAC     120

TCGGAATCGA AACTGGAACT GGAGCACAGC GATTCGGATA ATCAAGATGA GAAGTCCAAC     180

GCTAAGTTGG CGGAACGTCC TGAAGCCAAG CCAGAAGAAG ATGAAGAACT CAATGATCAA     240

GGCGAGAGGT ACATCTGCGG CTGGCCTCTG GTATTTCTCT TGTTAGCCAT GGTCTCCACA     300

GTCTTCATTG TCGCTTTGAG CAACACCATC ATCAGCACAG CAATCCCGGC CATCACAACA     360

GCGTTCAATA GTACCCGAGA TATTGGCTGG TACAACTCTG GAGAAGCTCT TGCAGCCACT     420

GCCTTCCAAC TACCTTTCGG GCGAGCGTAT CTCTTGATGG ACCTGAAGTG GACTTTCCTC     480

GTCTCACTGG CCTTATATCT GATCGGCAGC CTGATCTGTG GTGTGGCAAA CTCTTCTGAG     540

CTTCTCATTT TTGGCCGATC GATTGCAGGA GTTGGCAACG CTGGCGTCTT CGCTGGCGTG     600

TTCATCATTA TTGCTCGAAA CGTTCCTCTG CGGAAACGCA CTTTATGCTG GATTGGTTGG     660

AGCGACTTTT GCCATTGCTG CTGTGCTGGA CCTGTCCTGG GTGGTATCTT TACTGACCGT     720
```

-continued

```
ATTAGCTGGA GGTGGTGTTT GTACAGTAAG TCTCTAGAAC CCGTGCACTT TATTCCGTTC    780

ATTGACACTT TTCAACAGTT AACCTGCCTA TCGGAGCTGT ACGTGTCGCA ATCATCATAT    840

TCCTCCTTCC ATCTCGTCCT GGCGAAAAGG CAGCAGAAGT CAAGGACCTG TCCTGGTGGC    900

AGTTCTTCCT AAAGCTCAAT CCTTTTGGGT CGGCTCTCCT ACTCGGTTCC CTGACGTGCT    960

TTTTCCTCGC CCTACAGTGG GGCGGCGGCG AATACCGTTG GAGTGCTGGT CGTGTCGTTG   1020

CTGTACTGGT GGTCTTCGCC GTCAGCTTCA TCGGATGGCT GGTTCTGCAA TACTTCCAAG   1080

GCGACGAAGC CACACTGCCA TTTAACGTTG CAAAACAGCG TACCGTTGGT GGTGCCTCTA   1140

TCTACACTCT GCATCTGAGC GCCGCATTTG GACTCGTCAT ATACTATCTG CCTCTCTGGT   1200

GAGTTGATTC ATGAGCATGC ACTGGGCTCA CGAACTGACA TTATGAAGGT TTCAAGCAGT   1260

ACGATCTGAC AGTGCCGAAG CTGCTGGTCT CAAGCAACTT GGCATCGTCA TCTCGCTCAC   1320

TCTCTCGTCA ATTGCAGCTG GCGGTGCTGT TGTAAAAATA GGATATTACT ATCCTTTCAT   1380

TTACGCCGGA ACGGTCTTAT GCAGCATCGG CTCTGGCTTG CTTTACACGA TCACACTCGA   1440

TACACCGCAA TGGGATATGT AAGTAATCGA GCTCCGACTG AATTTGAACA TTTCTAACGC   1500

ATGACAGTAT CGGTTATTCG ATCGTATTCG CCATTGGAAT CGGCGTCAGT CTCGAGCAAT   1560

CCAACGTTGC TGTCCAGACT GTCCTGCCCG ATGCTCAGAT ACCAGCAGGA ACAAGCTTGG   1620

TTCTGTTCGT CCGACTACTT GGATCAGCAA TCCCCGGACC CATCGGACAG AGTGTACTCC   1680

AGACAACACT TGCCAGTAGG CTAGGGACTG AGGTCGCAGA GCAAGCATAT GGTGGTACCG   1740

GAGCAACTGA ATCCGCTCA AAGCTCGACA ACATTTTTGG AGCTGGCACA CCTGAAGCTC   1800

GAGATGCCCT TGACGCTTTC AACGATTCTG TGACGAAGAT CTTCATGGTC GCAATCATAG   1860

TCTCATGTCT GAGTGCGCTG CCTCTTCCCC TCATCGAGCT CAAGAGCGTC AAGCGTGAGA   1920

AACGAGACAA CGAAGACGCC AAAGAAGGCA AGAAAACTAA TGGGACGACG CGTGAGATAG   1980

AAGATCCAGA GAAGGGGCAG AGTGCAGAGA TCGTGGGCAA AGCAGTGTGA GATGTGGCAT   2040

CAGACCGAGC GACGATTTTA TAGACATTGT AGCGAGCTGT TACGACTAAC GCATGTACCC   2100

AACAGAGTGT GTGGCTCAGA GGCAATAGAG CTTTGCGACG ATAATAAACC AAGAATTTTA   2160

ATGGCTACGA GTCCTCTCAA AACCTCGCCG GA                                 2192
```

(2) INFORMATION FOR SEQ ID NO:2:

(i) SEQUENCE CHARACTERISTICS:
        (A) LENGTH: 1892 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:2:

```
CATACATTGA CAATGACGAG CCCAGCGCGA TCAACGCATA CTGATACAGA GTCTCACGAC     60

GTCGTAAAGA GCGACTCGGA ATCGAAACTG GAACTGGAGC ACAGCGATTC GGATAATCAA    120

GATGAGAAGT CCAACGCTAA GTTGGCGGAA CGTCCTGAAG CCAAGCCAGA AGAAGATGAA    180

GAACTCAATG ATCAAGGCGA GAGGTACATC TGCGGCTGGC CTCTGGTATT TCTCTTGTTA    240

GCCATGGTCT CCACAGTCTT CATTGTCGCT TTGAGCAACA CCATCATCAG CACAGCAATC    300

CCGGCCATCA CAACAGCGTT CAATAGTACC CGAGATATTG GCTGGTACAA CTCTGGAGAA    360
```

```
GCTCTTGCAG CCACTGCCTT CCAACTACCT TTCGGGCGAG CGTATCTCTT GATGGACCTG      420

AAGTGGACTT TCCTCGTCTC ACTGGCCTTA TATCTGATCG GCAGCCTGAT CTGTGGTGTG      480

GCAAACTCTT CTGAGCTTCT CATTTTTGGC CGATCGATTG CAGGAGTTGG CAACGCTGGC      540

GTCTTCGCTG GCGTGTTCAT CATTATTGCT CGAAACGTTC CTCTGCGGAA ACGCACTTTA      600

TGCTGGATTG GTTGGAGCGA CTTTTGCCAT TGCTGCTGTG CTGGACCTGT CCTGGGTGGT      660

ATCTTTACTG ACCGTATTAG CTGGAGGTGG TGTTTGTACA TTAACCTGCC TATCGGAGCT      720

GTACGTGTCG CAATCATCAT ATTCCTCCTT CCATCTCGTC CTGGCGAAAA GGCAGCAGAA      780

GTCAAGGACC TGTCCTGGTG GCAGTTCTTC CTAAAGCTCA ATCCTTTTGG GTCGGCTCTC      840

CTACTCGGTT CCCTGACGTG CTTTTTCCTC GCCCTACAGT GGGGCGGCGG CGAATACCGT      900

TGGAGTGCTG GTCGTGTCGT TGCTGTACTG GTGGTCTTCG CCGTCAGCTT CATCGGATGG      960

CTGGTTCTGC AATACTTCCA AGGCGACGAA GCCACACTGC CATTTAACGT TGCAAAACAG     1020

CGTACCGTTG GTGGTGCCTC TATCTACACT CTGCATCTGA GCGCCGCATT TGGACTCGTC     1080

ATATACTATC TGCCTCTCT GGTTTCAAGC AGTACGATCT GACAGTGCCG AAGCTGCTGGT     1140

CTCAAGCAA CTTGGCATCG TCATCTCGCT CACTCTCTCG TCAATTGCAG CTGGCGGTGCT     1200

GTTGTAAAA ATAGGATATT ACTATCCTTT CATTTACGCC GGAACGGTCT TATGCAGCATC     1260

GGCTCTGGC TTGCTTTACA CGATCACACT CGATACACCG CAATGGGATA TTATCGGTTAT     1320

TCGATCGTA TTCGCCATTG GAATCGGCGT CAGTCTCGAG CAATCCAACG TTGCTGTCCAG     1380

ACTGTCCTG CCCGATGCTC AGATACCAGC AGGAACAAGC TTGGTTCTGT TCGTCCGACTA     1440

CTTGGATCA GCAATCCCCG GACCCATCGG ACAGAGTGTA CTCCAGACAA CACTTGCCAGT     1500

AGGCTAGGG ACTGAGGTCG CAGAGCAAGC ATATGGTGGT ACCGGAGCAA CTGAAATCCGC     1560

TCAAAGCTC GACAACATTT TTGGAGCTGG CACACCTGAA GCTCGAGATG CCCTTGACGCT     1620

TTCAACGAT TCTGTGACGA AGATCTTCAT GGTCGCAATC ATAGTCTCAT GTCTGAGTGCG     1680

CTGCCTCTT CCCCTCATCG AGCTCAAGAG CGTCAAGCGT GAGAAACGAG ACAACGAAGAC     1740

GCCAAAGAA GGCAAGAAAA CTAATGGGAC GACGCGTGAG ATAGAAGATC CAGAGAAGGGG     1800

CAGAGTGCA GAGATCGTGG GCAAAGCAGT GTGAGATGTG GCATCAGACC GAGCGACGATT     1860

TTATAGACA TTGTAGCGAG CTGTTACGAC TAA                                   1892
```

(2) INFORMATION FOR SEQ ID NO:3:

(i) SEQUENCE CHARACTERISTICS:
        (A) LENGTH: 606 amino acids
        (B) TYPE: amino acid
        (C) STRANDEDNESS: single
        (D) TOPOLOGY: linear (ii) MOLECULE TYPE: protein (iii) HYPOTHETICAL: YES (iv) ANTI-SENSE: NO (xi) SEQUENCE DESCRIPTION: SEQ ID NO:3:

```
Met Thr Ser Pro Ala Arg Ser Thr His Thr Asp Thr Glu Ser His Asp
 1               5                  10                  15

Val Val Lys Ser Asp Ser Glu Ser Lys Leu Glu Leu Glu His Ser Asp
             20                  25                  30

Ser Asp Asn Gln Asp Glu Lys Ser Asn Ala Lys Leu Ala Glu Arg Pro
         35                  40                  45
```

-continued

```
Glu Ala Lys Pro Glu Glu Asp Glu Leu Asn Asp Gln Gly Glu Arg
 50                  55                  60

Tyr Ile Cys Gly Trp Pro Leu Val Phe Leu Leu Ala Met Val Ser
 65                  70                  75                  80

Thr Val Phe Val Phe Ile Val Ala Leu Ser Asn Thr Ile Ile Ser Thr
                 85                  90                  95

Ala Ile Pro Ala Ile Thr Thr Ala Phe Asn Arg Asp Ile Gly Trp Tyr
            100                 105                 110

Asn Ser Gly Glu Ala Leu Ala Ala Thr Ala Phe Gln Leu Pro Phe Gly
        115                 120                 125

Arg Ala Tyr Leu Leu Met Asp Leu Lys Trp Thr Phe Leu Val Ser Leu
    130                 135                 140

Ala Leu Tyr Leu Ile Gly Ser Leu Ile Cys Gly Val Ala Asn Ser Ser
145                 150                 155                 160

Glu Leu Leu Ile Phe Gly Arg Ser Ile Ala Gly Val Gly Asn Ala Gly
                165                 170                 175

Val Phe Ala Gly Val Phe Ile Ile Ala Arg Asn Val Pro Leu Arg
            180                 185                 190

Lys Arg Thr Leu Cys Trp Ile Gly Trp Ser Asp Phe Cys His Cys Cys
    195                 200                 205

Cys Ala Gly Pro Val Leu Gly Gly Ile Phe Thr Asp Arg Ile Ser Trp
210                 215                 220

Arg Trp Cys Leu Tyr Ile Asn Leu Pro Ile Gly Ala Val Arg Val Ala
225                 230                 235                 240

Ile Ile Ile Phe Leu Leu Pro Ser Arg Pro Gly Glu Lys Ala Ala Glu
                245                 250                 255

Val Lys Asp Leu Ser Trp Trp Gln Phe Phe Leu Lys Leu Asn Pro Phe
            260                 265                 270

Gly Ser Ala Leu Leu Leu Gly Ser Leu Thr Cys Phe Phe Leu Ala Leu
        275                 280                 285

Gln Trp Gly Gly Gly Glu Tyr Arg Trp Ser Ala Gly Arg Val Val Ala
    290                 295                 300

Val Leu Val Val Phe Ala Val Ser Phe Ile Gly Trp Leu Val Leu Gln
305                 310                 315                 320

Tyr Phe Gln Gly Asp Glu Ala Thr Leu Pro Phe Asn Val Ala Lys Gln
                325                 330                 335

Arg Thr Val Gly Gly Ala Ser Ile Tyr Thr Leu His Leu Ser Ala Ala
            340                 345                 350

Phe Gly Leu Val Ile Tyr Tyr Leu Pro Leu Trp Phe Gln Ala Val Arg
        355                 360                 365

Ser Asp Ser Ala Glu Ala Ala Gly Leu Lys Gln Leu Gly Ile Val Ile
    370                 375                 380

Ser Leu Thr Leu Ser Ser Ile Ala Ala Gly Ala Val Val Lys Ile
385                 390                 395                 400

Gly Tyr Tyr Tyr Pro Phe Ile Tyr Ala Gly Thr Val Leu Cys Ser Ile
                405                 410                 415

Gly Ser Gly Leu Leu Tyr Thr Ile Thr Leu Asp Thr Pro Gln Trp Asp
            420                 425                 430

Ile Ile Gly Tyr Ser Ile Val Phe Ala Ile Gly Ile Gly Val Ser Leu
        435                 440                 445

Glu Gln Ser Asn Val Ala Val Gln Thr Val Leu Pro Asp Ala Gln Ile
    450                 455                 460
```

-continued

```
Pro Ala Gly Thr Ser Leu Val Leu Phe Val Arg Leu Leu Gly Ser Ala
465                 470                 475                 480

Ile Pro Gly Pro Ile Gly Gln Ser Val Leu Gln Thr Thr Leu Ala Ser
            485                 490                 495

Arg Leu Gly Thr Glu Val Ala Glu Gln Ala Tyr Gly Gly Thr Gly Ala
            500                 505                 510

Thr Glu Ile Arg Ser Lys Leu Asp Asn Ile Phe Gly Ala Gly Thr Pro
        515                 520                 525

Glu Ala Arg Asp Ala Leu Asp Ala Phe Asn Asp Ser Val Thr Lys Ile
        530                 535                 540

Phe Met Val Ala Ile Ile Val Ser Cys Leu Ser Ala Leu Pro Leu Pro
545                 550                 555                 560

Leu Ile Glu Leu Lys Ser Val Lys Arg Glu Lys Arg Asp Asn Glu Asp
            565                 570                 575

Ala Lys Glu Gly Lys Lys Thr Asn Gly Thr Thr Arg Glu Ile Glu Asp
            580                 585                 590

Pro Glu Lys Gly Gln Ser Ala Glu Ile Val Gly Lys Ala Val
            595                 600                 605
```